(12) United States Patent
Gemeinhart et al.

(10) Patent No.: US 9,457,101 B2
(45) Date of Patent: Oct. 4, 2016

(54) HYDROGELS FOR DELIVERY OF THERAPEUTIC POLYPEPTIDES

(71) Applicant: The Board of Trustees of the University of Illinois, Urbana, IL (US)

(72) Inventors: Richard Gemeinhart, Chesterton, IN (US); Jason Buhrman, Glendale Heights, IL (US); Jamie Rayahin, Des Plaines, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/405,701

(22) PCT Filed: Jun. 6, 2013

(86) PCT No.: PCT/US2013/044510
§ 371 (c)(1),
(2) Date: Apr. 22, 2015

(87) PCT Pub. No.: WO2013/184915
PCT Pub. Date: Dec. 12, 2013

(65) Prior Publication Data
US 2015/0258211 A1    Sep. 17, 2015

Related U.S. Application Data

(60) Provisional application No. 61/656,040, filed on Jun. 6, 2012.

(51) Int. Cl.
| | | |
|---|---|---|
| A61K 38/00 | (2006.01) | |
| A61B 6/00 | (2006.01) | |
| A61K 47/48 | (2006.01) | |
| A61K 9/06 | (2006.01) | |
| A61K 49/00 | (2006.01) | |
| A61K 47/32 | (2006.01) | |

(52) U.S. Cl.
CPC ........... *A61K 47/48784* (2013.01); *A61K 9/06* (2013.01); *A61K 47/32* (2013.01); *A61K 47/48215* (2013.01); *A61K 49/0047* (2013.01); *A61K 49/0091* (2013.01); *A61K 38/00* (2013.01)

(58) Field of Classification Search
None
See application file for complete search history.

Primary Examiner — Jeanette Lieb
(74) Attorney, Agent, or Firm — Botkin & Hall, LLP

(57) ABSTRACT

Disclosed herein is a hydrogel composition comprising a polymer covalently linked to glutathione (GSH). Also disclosed herein is a method for providing localized delivery of one or more agents in a subject suffering from a disease. The method comprises administering to the subject a GST/GSH affinity hydrogel comprising a therapeutically effective amount of the one or more agents.

17 Claims, 22 Drawing Sheets

HYDROGELS FOR DELIVERY OF THERAPEUTIC POLYPEPTIDES

CROSS REFERENCE TO RELATED APPLICATION

This application claims priority to PCT Application No. PCT/U.S. Ser. No. 13/044,510, filed Jun. 6, 2013, which claims priority to U.S. Prov. App. No. 61/656,040, filed Jun. 6, 2012, both of which are hereby incorporated by reference.

STATEMENT OF GOVERNMENT INTEREST

This invention was made with government support under Grant Nos. NS055095 and C06 RR15482 awarded by NIH. The government has certain rights in the invention.

TECHNICAL FIELD

The present invention relates to polymers and methods of using such polymers for delivery of therapeutic polypeptides to a subject in need thereof.

SEQUENCE LISTING

Filed electronically herewith a Sequence Listing named 2596_002_Sequencelistingasfiled.txt, created on Dec. 4, 2014 which is 3 Kilobytes in size.

BACKGROUND

Targeted and localized delivery of drugs is a goal of the medical and pharmaceutical industries. In targeted drug delivery the aim is to optimize drug efficacy by localizing its therapeutic effect to the diseased or infected site or organ of action. A successfully targeted therapeutic provides a significant reduction in drug toxicity, reduction of the drug dose, and increased treatment efficacy as compared to, for example, those therapeutics that may not be specifically targeted to a diseased tissue or organ. Decreased bioavailability of drugs is often a consequence of their non-specific nature. Further, drug efficacy depends upon the ability of the drug to reach its target in sufficient quantity to maintain therapeutic levels for the desired time period. Accordingly, there is a need for new compositions and methods for localized and targeted delivery of therapeutics that are not subject to the same physiological impediments often encountered by, for example, drugs that do not efficaciously impart their therapeutic effect to their intended target.

SUMMARY

The present invention is directed a hydrogel composition comprising a polymer covalently linked to glutathione (GSH). The polymer may comprise one or more monomers. The one or more monomers may be selected from the group consisting of acryl monomers, acryl macromers, and the combination thereof. The one or more monomers may also be selected from the group consisting of poly(ethylene glycol) diacrylate (PEGDA), hyaluronic acid acrylate, poly (acrylamide), poly(acrylic acid), copolymers thereof, and combinations thereof. The one or more monomers may be PEGDA. A ratio of PEGDA to GSH (PEGDA:GSH) may be from 1:1 to 5:1.

The hydrogel may be a microsphere. One or more agents may be immobilized on a surface of the microsphere. The surface may be selected from the group consisting of an interior surface of the microsphere, an exterior surface of the microsphere, and the combination thereof. The surface may be the exterior surface of the microsphere. The one or more agents may be substantially prevented from interacting with the interior of the microsphere. An amount of the one or more agents immobilized on the exterior surface of the microsphere may be greater than an amount of a single monolayer of the one or more agents being immobilized on the exterior surface of the microsphere.

The one or more agents may be one or more polypeptides covalently linked to glutathione s-transferase (GST). The one or more polypeptides may be linked to GST via a recognition site for a protease. The protease may be selected from the group consisting of a matrix metalloprotease (MMP), thrombin, urokinase plasminogen activator, and combinations thereof.

The one or more polypeptides may comprise one or more therapeutic polypeptides. The one or more therapeutic polypeptides may be selected from the group consisting of an anti-angiogenic polypeptide, anti-proliferative polypeptide, a bactericidal polypeptide, and combinations thereof. The bactericidal polypeptide may be melittin.

The present invention is also directed to a bactericidal delivery system comprising a GST-Melittin polypeptide immobilized on PEGDA:GSH hydrogel microspheres. Release of melittin from the PEGDA:GSH hydrogel microspheres may be activated by thrombin.

The present invention is further directed to a method for providing localized delivery of one or more agents in a subject suffering from a disease. The method may comprise administering to the subject a GST/GSH affinity hydrogel comprising a therapeutically effective amount of the one or more agents. The disease may be selected from the group consisting of a vascular disease and a proliferative disease. The vascular disease may be selected from the group consisting of diabetic retinopathy and age-related macular degeneration.

The one or more agents may be one or more therapeutic polypeptides. The one or more therapeutic polypeptides may be selected from the group consisting of an anti-angiogenic polypeptide, anti-proliferative polypeptide, a bactericidal polypeptide, and combinations thereof. The one or more agents may be selectively released from the hydrogel via a protease. The protease may be selected from the group consisting of a matrix metalloprotease (MMP), thrombin and urokinase plasminogen activator. The protease may be present at a site of the localized delivery before administration of the hydrogel to the subject. The disease may promote the presence of the protease at the localized delivery site, thereby linking a rate of release of the one or more agents from the hydrogel to the disease.

DETAILED DESCRIPTION

Figure 1:
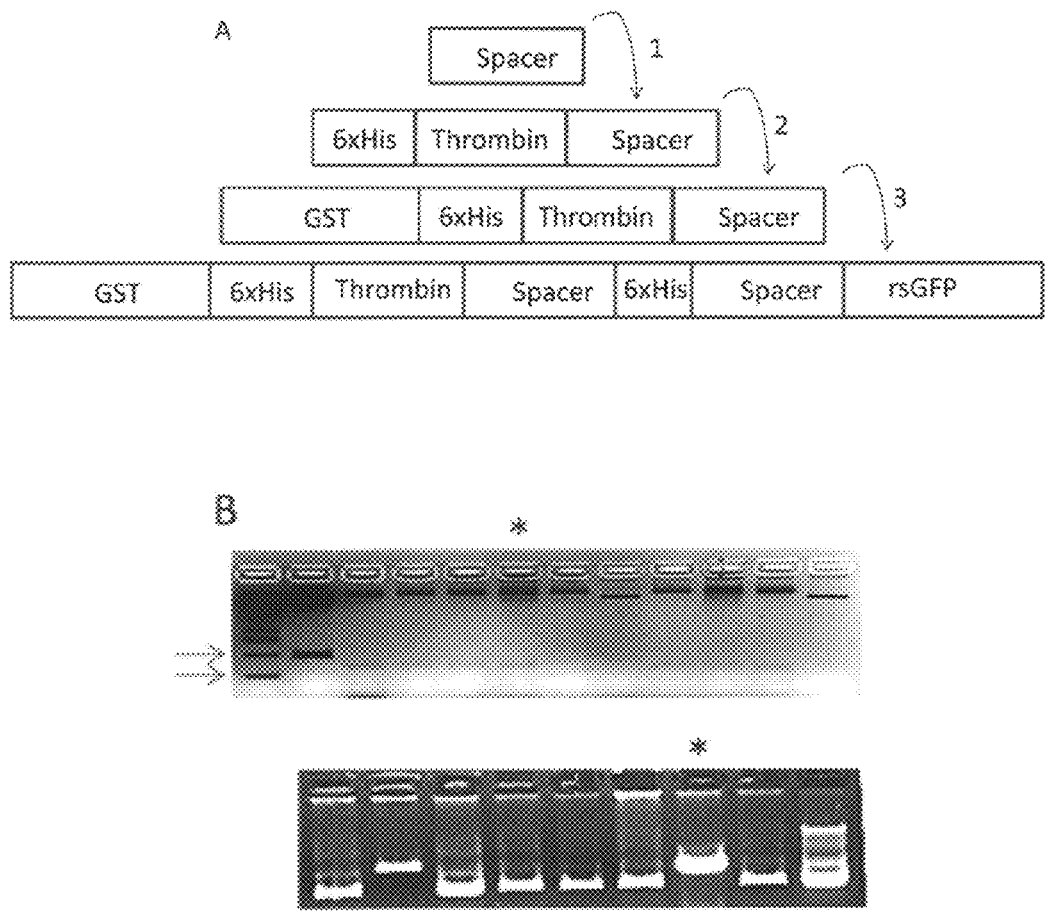
FIG. 1 shows the cloning and purification of GST-GFP. A: Schematic of vector construction. (1) A spacer was cloned into the pET 15b vector/plasmid in proximity to the hexahistidine tag and thrombin site, pJB-HTS. This fragment was cloned from the pET 15b vector into the pGex-6p-1 vector to add a GST upstream, pJB-GST-HTS. Red shifted GFP was cloned into pJB-GST-THS along with another spacer, and a separate 6xhis tag, pJB-GST-HTS-HS-GFP. B: Gel electrophoresis screening of DNA prepared from colonies following step 1. pJB-HTS were digested with BglII/HindIII (top) the loss of a 500 bp band (lane 1) appearance of a 318 bp digestion fragment indicated positive colony for spacer insertion. Arrows indicate 500 bp and 250 bp bands on marker. 7/10 colonies had positive insertion, and colony 7 (asterisk) was chosen for sequencing and further cloning. The HTS fragment from pJB-HTS was amplified by PCR and cloned into pGex-6p-1 to form pJB-GST-HTS. DNA was digested with NcoI to screen for positive for insertions. Positive clones would result in linearization of supercoiled DNA, and 2/10 colonies screened showed this feature. One was chosen for sequencing and further cloning (asterisk). C: Basal GFP expression of a pJB-GST-HTS-HS-GFP containing colony was observed microscopically (brightfield overlaid with epifluoresence) with the scale bar indicating 100 μm. After induction, bacteria express significant green color under UV illumination (bottom) indicating high levels of GFP expression. D: GST-GFP electrophoresed as predicted for the known molecular weight (2) before and (3) after cleavage with thrombin as compared to the (1) molecular weight ladder with arrows indicating 55 kDa, 35 kDa, 25 kDa.
Figure 1:
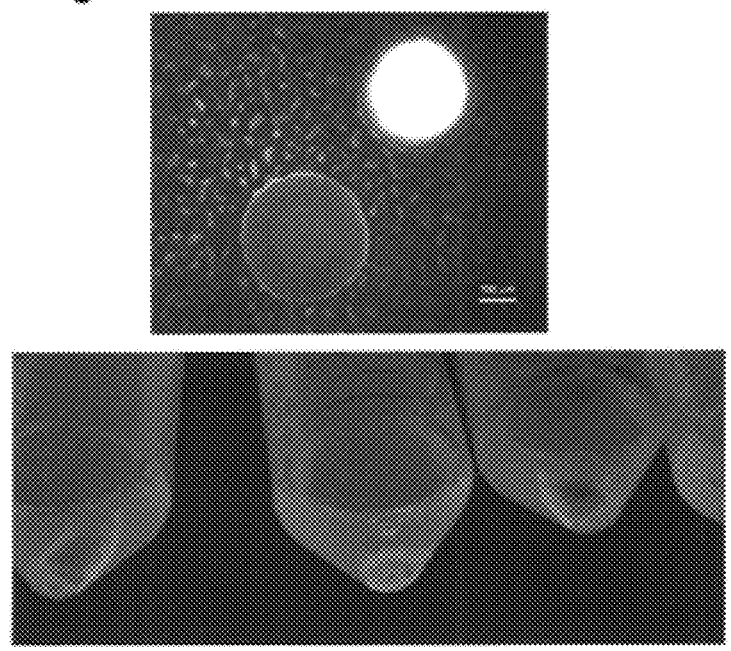
Figure 1:
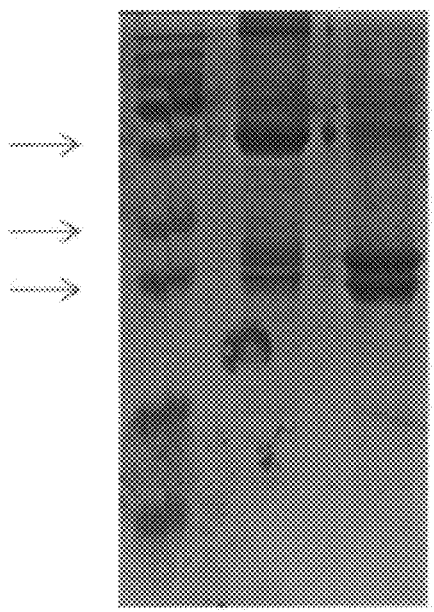

The present invention relates to hydrogel compositions and methods for delivering an agent to a subject in need thereof using the same. The hydrogel composition may include poly(ethylene glycol) diacrylate (PEGDA) and glutathione (GSH). The GSH may be covalently linked to the PEGDA. A ratio of PEGDA to GSH (PEGDA:GSH) may be about 1:1 to about 5:1. In some embodiments, the PEGDA:GSH ratio may be 5:1.

The hydrogel composition may further include an agent immobilized on a surface of the hydrogel. In some embodiments, the hydrogel may be a microsphere, and therefore, the agent may be immobilized on the surface of such a microsphere. The agent may be a therapeutic polypeptide that is covalently linked to glutathione s-transferase (GST). Accordingly, the therapeutic polypeptide is immobilized on the surface of the hydrogel via an interaction between GST and GSH. The therapeutic polypeptide may be, for example, an anti-angiogenic polypeptide (e.g., SEQ ID NOS:3 and 4) or a bactericidal polypeptide (e.g., melittin).

A recognition site for a protease may be located between the therapeutic polypeptide and GST. As such, the protease recognition site links the therapeutic polypeptide and GST, and when the protease acts upon its recognition site, the therapeutic polypeptide is released from GST and thus the surface of the hydrogel. The protease may be, for example, a matrix metalloprotease (MMP), thrombin, or urokinase plasminogen activator (uPA).

The present invention also relates to a method for providing local delivery of the agent to a subject suffering from a disease. The disease may be, for example, a vascular disease (e.g., diabetic retinopathy and age-related macular degeneration) or a proliferative disease (e.g., cancer). Such a method may include administering to the subject the hydrogel composition, in which a therapeutically effective amount of the agent has been immobilized to the hydrogel.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "may," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

A "peptide," "protein," or "polypeptide" as used herein may mean a linked sequence of amino acids and may be natural, synthetic, or a modification or combination of natural and synthetic.

Variant may be defined as a peptide or polypeptide that differs in amino acid sequence by the insertion, deletion, or conservative substitution of amino acids, but retain at least one biological activity. Variants may be a fragment thereof. Representative examples of "biological activity" include the ability to be bound by a specific antibody or to promote an immune response. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values may result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

The term "subject" or "patient" as used herein interchangeably means any vertebrate, including, but not limited to, a mammal (e.g., cow, pig, camel, llama, horse, goat, rabbit, sheep, hamster, guinea pig, cat, dog, rat, and mouse, a non-human primate (for example, a monkey, such as cynomolgous or rhesus monkey, chimpanzee, etc.)) and a human. In some embodiments, the subject or patient may be a human or a non-human. The subject or patient may be undergoing other forms of treatment. In some embodiments, the subject or patient may be a human at risk for developing or already having one or more diseases.

The term "effective dosage" or "effective amount" as used herein interchangeably means a dosage or an amount of an agent effective for periods of time necessary, to achieve the desired therapeutic result. An effective dosage or amount may be determined by a person skilled in the art and may vary according to factors such as the disease state, age, sex, and weight of the individual, and the ability of the agent to elicit the desired response in the individual.

2. Hydrogel Composition

Provided herein is a hydrogel composition. The hydrogel composition includes PEGDA and GSH, which may be linked together and used to form a hydrogel. In other embodiments, the hydrogel composition may include one or more monomer(s), for example, PEGDA, hyaluronic acid, polyacrylamide, poly(acrylic acid), and GSH. The linkage may be a covalent linkage. The hydrogel may be homogenized into pieces or may be formed into microspheres. An agent may be tethered or immobilized on a surface or exterior of the hydrogel. The agent may be releasable from the hydrogel. Such release may be mediated by or accomplished via a protease acting on the agent.

a. PEGDA:GSH Ratio

The PEGDA and GSH may be present in the hydrogel in differing amounts relative to one another. Particularly, the hydrogel may include a ratio of PEGDA to GSH (PEGDA:

GSH) of about 1:0.5 to about 7:1. In other embodiments, the PEGDA:GSH ratio may be about 1:1 to about 5:1. In still other embodiments, the PEGDA:GSH ratio may be about 1:1, 2:1, 3:1, 4:1, or 5:1 in the hydrogel.

b. Microsphere

The hydrogel may be a microsphere. The microsphere may have a diameter of about 1 microns to about 100 microns. In other embodiments, the diameter may be about 20 microns to about 80 microns. In still other embodiments, the diameter may be about 25 microns to about 65 microns. The diameter may be about 25 microns, 26 microns, 27 microns, 28 microns, 29 microns, 30 microns, 31 microns, 32 microns, 33 microns, 34 microns, 35 microns, 36 microns, 37 microns, 38 microns, 39 microns, 40 microns, 41 microns, 42 microns, 43 microns, 44 microns, 45 microns, 46 microns, 47 microns, 48 microns, 49 microns, 50 microns, 51 microns, 52 microns, 53 microns, 54 microns, 55 microns, 56 microns, 57 microns, 58 microns, 59 microns, 60 microns, 61 microns, 62 microns, 63 microns, 64 microns, or 65 microns.

The microsphere may have a mesh size of about 3.3 nm to about 15 nm. In other embodiments, the mesh size may be about 4.0 nm to about 10 nm. In still other embodiments, the mesh size may be about 4.3 nm to about 5.0 nm or about 4.0 to 5.2 nm. The mesh size may be about 4.3 nm, 4.4 nm, 4.5 nm, 4.6 nm, 4.7 nm, 4.8 nm, 4.9 nm, or 5.0 nm.

The microsphere may have a surface area. The surface area may be about 5,000 $\mu m^2$ to about 20,000 $\mu m^2$. In other embodiments, the surface area may be about 11,000 $\mu m^2$ to about 14,000 $\mu m^2$. In still other embodiments, the surface area may be out 11,000 $\mu m^2$, 11,500 $\mu m^2$, 12,000 $\mu m^2$, 12,500 $\mu m^2$, 13,000 $\mu m^2$, 13,500 $\mu m^2$, or 14,000 $\mu m^2$.

c. Agent

The hydrogel composition may also include one or more agents. The hydrogel composition may include two or more different agents. The agent may be tethered or immobilized on the surface or exterior of the hydrogel. Alternatively, the agent may be immobilized in the interior of the hydrogel or a combination of the interior and exterior of the hydrogel. The agent may be an amino acid sequence. The amino acid sequence may be a protein, a polypeptide, a peptide, a variant thereof, a fragment thereof, or a combination thereof. The amino acid sequence may be recombinant. The amino acid sequence may be modified. For example, the amino acid sequence may be expressed in vivo, whereby it is post-translationally modified. Modifications of the amino acid sequence may include the attachment of one or more sugars to the amino acids sequence. For example, chondroitin or a sulfated glycosaminoglycan may be attached to the agent. The sulfated glycosaminoglycan may be chondroitin sulfate. The chondroitin or chondroitin sulfate may be attached to the agent via a serine residue, for example.

The polypeptide may be a therapeutic polypeptide. The therapeutic polypeptide may promote wound healing. The therapeutic polypeptide may also be effective in treatments for cancer, bacterial infection, and/or arthritis. The therapeutic polypeptide may be an anti-angiogenic polypeptide, a cell toxic polypeptide, a cell lytic polypeptide, an anti-proliferative polypeptide, a bactericidal polypeptide, or combinations thereof. The polypeptide may be a growth factor, a TNF-Related Apoptosis Inducing Ligand (TRAIL), a trans-activator of transcription (TAT), or a Low density lipoprotein receptor-related protein (LRP). The polypeptide or peptide may contain an Arg-Gly-Asp amino acid motif, which is a common element cellular recognition. The therapeutic polypeptide may be melittin, which may comprise the amino acid sequence GIGAVLKVLTTGLPAL-ISWIKRKRQ (SEQ ID NO:2). In other embodiments, the therapeutic polypeptide may be a cell toxic peptide having the amino acid sequence KWKLFKKIGAVLKVL (SEQ ID NO:3) or a collagen derived peptide that inhibits angiogenesis and having the amino acid sequence CNYYSNS (SEQ ID NO:4). The therapeutic polypeptide may be interleukin 1 receptor antagonist (IL1-RA) or angiostatin.

The agent may be linked to GST to form a GST-fusion agent, which may be a GST-fusion protein. The linkage between the agent and GST may be covalent. The linkage between the agent and GST may comprise one or more amino acids. The one or more amino acids may comprise a recognition site for a protease. The protease may cleave or sever the linkage between the agent and GST. The hydrogel composition may include two or more different GST-fusion agents. The GST-fusion agents may be tethered or immobilized on the surface or exterior of the hydrogel. Alternatively, the GST-fusion agents may be immobilized in the interior of the hydrogel or a combination of the interior and exterior of the hydrogel.

GST binds GSH with high affinity and specificity. Accordingly, the interaction between GST and GSH may promote or facilitate tethering of the agent (i.e., attached to GST) to the hydrogel (i.e., includes GSH). In the presence of an amount of GSH greater than the binding affinity of GST for GSH, the agent may be released from the hydrogel because the additional GSH competes with the GSH of the hydrogel for binding to the GST linked to the agent. In other embodiments, the protease cleaves the linkage between GST and the agent such that GST remains bound to the GSH of the hydrogel and the agent is released from GST. Accordingly, the agent is selectively released from the hydrogel.

d. Protease

The agent may be tethered or immobilized to the hydrogel. The agent may be selectively released from the hydrogel via the action of a protease. When the hydrogel is a microsphere, the release capacity from the microsphere via action of the protease may be about $6.5 \times 10^8$ molecules to about $13.5 \times 10^8$ molecules. In other embodiments, the release capacity may be about $7.4 \times 10^8$ molecules to about $12.4 \times 10^8$ molecules. In still other embodiments, the release capacity may be about $7.4 \times 10^8$, $7.5 \times 10^8$, $7.6 \times 10^8$, $7.7 \times 10^8$, $7.8 \times 10^8$, $7.9 \times 10^8$, $8.0 \times 10^8$, $8.1 \times 10^8$, $8.2 \times 10^8$, $8.3 \times 10^8$, $8.4 \times 10^8$, $8.5 \times 10^8$, $8.6 \times 10^8$, $8.7 \times 10^8$, $8.8 \times 10^8$, $8.9 \times 10^8$, $9.0 \times 10^8$, $9.1 \times 10^8$, $9.2 \times 10^8$, $9.3 \times 10^8$, $9.4 \times 10^8$, $9.5 \times 10^8$, $9.6 \times 10^8$, $9.7 \times 10^8$, $9.8 \times 10^8$, $9.9 \times 10^8$, $10.0 \times 10^8$, $10.1 \times 10^8$, $10.2 \times 10^8$, $10.3 \times 10^8$, $10.4 \times 10^8$, $10.5 \times 10^8$, $10.6 \times 10^8$, $10.7 \times 10^8$, $10.8 \times 10^8$, $10.9 \times 10^8$, $11.0 \times 10^8$, $11.1 \times 10^8$, $11.2 \times 10^8$, $11.3 \times 10^8$, $11.4 \times 10^8$, $11.5 \times 10^8$, $11.6 \times 10^8$, $11.7 \times 10^8$, $11.8 \times 10^8$, $11.9 \times 10^8$, $12.0 \times 10^8$, $12.1 \times 10^8$, $12.2 \times 10^8$, $12.3 \times 10^8$, or $12.4 \times 10^8$ molecules.

The protease may cleave or sever an amino acid sequence between GST and the agent. The protease may penetrate the hydrogel and cleave the agent from the GST. The protease may be a matrix metalloprotease (MMP), for example, matrix metalloprotease 9. The protease may also be thrombin, cathepsin, tissue plasminogen activator (tPA), urokinase plasminogen activator (uPA), or elastase. The protease may recognize and cleave a specific amino acid sequence, which may be native to GST and/or the agent. The protease may recognize and cleave a specific amino acid sequence that is genetically engineered into, or between, the GST and/or the agent. For example, a metalloprotease may recognize and cleave the following sequence: GPLGVRGS (SEQ ID NO:5).

3. Method for Delivering the Agent

Also provided herein is a method for localized delivery of the agent to a subject suffering from a disease. The method may include administering to the subject the hydrogel composition. The hydrogel composition may be administered orally to the subject and/or contacted directly with the target cell, tissue, or organ. The composition may be further formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Compositions for intravenous administration may be in sterile isotonic aqueous buffer. Where necessary, the composition may also include a solubilizing agent and a local anesthetic such as lignocaine to ease pain at the site of the injection.

The hydrogel composition may include a therapeutically effective amount of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which toxic or detrimental effects, if any, of the composition are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount. As described above, the agent may be selectively releasable from the hydrogel. Selective release of the agent from the hydrogel may be mediated by the protease. The protease may be present at a site of the localized delivery, and the presence of the protease at the delivery site may be promoted by the disease. Accordingly, a rate of release of the agent from the hydrogel may correspond to levels of the protease, which in turn, protease levels may be impacted or driven by progression of the disease.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in subjects.

The disease may be a proliferative disease, a vascular disease, or a cardiovascular disease. The proliferative disease may be a cancer while the vascular disease may be diabetic retinopathy or age-related macular degeneration. In some embodiments, the disease may be a bacterial infection, wound healing, or arthritis.

To treat a diseased or infected cell, tissue or organ, the hydrogel composition may be placed in contact with diseased or infected cell, tissue or organ. For example, when the hydrogel composition system is shaped as a contact lens, the lens may simply be placed in the eye normally in order to deliver the agent. In order to effect accelerated healing, the hydrogel may be part of a bandage or may be adhered (e.g., by adhesives or sutures) to, or surgically placed into contact with, the diseased or infected cell, tissue or organ. If the hydrogel composition is placed internally in a patient, the hydrogel may be advantageously biodegradable.

Hydrogels may be considered to be disposable and may be replaced after a specified period of time, e.g., at least 0.5, 1, 1.5, 2, 2.5, 3, 3.5, 4, 4.5, 5, 7.5, 10, 15, or 24 hours. Alternatively, a hydrogel that has a depleted amount of one or more agents may be recycled or replaced.

The invention may be used in conjunction with healing many types of cells, tissues and organs, including, without limitation, ocular, oral, lung, digestive tract, skin, large intestine, small intestine, colon, and other infections and diseases to endothelial, mucosal, or epithelial tissues. In addition, the hydrogel may also act as a physical barrier to provide protection from mechanical abuse and to prevent adherence of the healing tissue to adjacent tissues. The use of hydrogels of the invention may also allow patients to be treated using fewer applications than with traditional methods. For example, a patient treated using the hydrogels of the invention may be able to be treated only once in a period of at least 48 hours.

In one embodiment, the wound is an ocular wound, e.g., in corneal epithelial, endothelial, or retinal tissue. The invention is of particular utility after vision correcting surgery, such as LASIK, PRK, or LASEK. Soft and collagen contact lenses may be utilized to minimize post-surgical epithelial trauma or infection and provide a stable healing environment. PRK typically requires a therapeutic contact lens for 3-4 days, and post-operative therapeutic drops are often prescribed. In the present invention, the hydrogel may be shaped as a contact lens that acts as a reservoir for the agent and may serve to protect the leading edge of wound healing from normal mechanical abuse and/or infection.

4. Kits

Also provided herein are kits for use with the methods and compositions disclosed herein. The kits may include reagents for forming the hydrogel composition. Particularly, the kit may include a polymer covalently linked to glutathione (GSH), such as a PEGDA:GSH hydrogel, and reagents for forming the GST-fusion agent. The reagents for forming the GST-fusion agent may be any of those reagents known in the art, for example, reagents for recombinant protein technology and the like. The kits also include controls and instructions for how to use the kit.

The present invention has multiple aspects, illustrated by the following non-limiting examples.

5. Examples

Example 1

Materials and Methods for Examples 2-6

Vectors. All cloning was clone in DH5alpha *E. coli* cells and all vectors conferred ampicillin resistance. The vector for protein production, pJB-GST-HTS-HS-GFP, was created by first cloning a 7 amino acid spacer fragment containing an XhoI site into pET-15b (Novagen) using sticky ligation and BamHI/XhoI sites. Colonies were mini-prepped by conventional SDS-precipitation and screened by BglII/HindIII (New England Biolabs [NEB]) digestion (FIG. 1B, lower panel). Colonies were confirmed by subsequent sequencing (ACGT). Primers were designed to fit in resulting vector, pJB-HTS upstream of the hexa-histidine tag (5/phos/CCATGGGCAGCAGCCATCATCAT (SEQ ID NO:6)), and downstream (AGCTGGAATTCCTAGTTATTGCTCAGCGGTGGC (SEQ ID NO:7)) (Integrated DNA technologies) of the spacer yielding a fragment containing a phosphorylated 5' end, an initiation codon, a hexa-histidine tag, a thrombin cleavable sequence, a spacer, a termination codon, and an EcoRI site. This fragment was digested with EcoRI (NEB) and ligated into pGex-6p1 (GE Healthcare) prepared by digestion with BamHI and blunting with Mung Bean Nuclease (NEB) to generate pJB-GST-HTS. Correct insertion yielded a novel NcoI site generated by ligation of the blunted ends, and NcoI (NEB) linearization of the supercoiled vector was used to determine correct insertion (FIG. 1B, lower panel). These clones were confirmed by DNA sequencing. Primers were designed to clone rsGFP from gWIZ-GFP (Aldevron) and extending a BamHI site, a hexa-histidine tag, another spacer region, the GFP, and an EcoRI site. pJB-GST-HTS and the PCR fragment were prepared by BamHI and EcoRI digestion (Fw: AAAGGATCCATCATCATCATCATCATGGTC-CGCTGGGCGTTCGTGGTATGGCTAG CAAAGGA-GAAGAACTC (SEQ ID NO:8), Rev: AAAGAATTCTCA-GTTGTACAGTTCATCCATGCCATG (SEQ ID NO:9)). Colonies were screened under UV microscopy for basal expression of GFP (FIG. 1C). DNA was sequenced from positive colonies containing the final product pJB-GST-HTS-HS-GFP.

Protein Expression and Purification. The vector, pJB-GST-HTS-HS-GFP was transformed into BL21 expression cells for expression and purification of GST-GFP protein. Protein was induced with 1 mM IPTG after cells reached an A595 of 0.5. Cells were removed to 25 degrees Celsius and were shaken overnight. Cells were spun at 4 degrees Celsius for 20 minutes to pellet, and resuspended in lysis buffer (50 mM $NaH_2PO_4$, 300 mM NaCl, 10 mM imidazole, pH 8). The suspension was freeze-thawed 3 times at −80 degrees Celsius, sonicated 3 times each for 15 seconds then spun at 12,000 revolutions per minute (RPM) for 30 minutes to pellet the insoluble material. The supernatents were removed and selected through a gravity flow nickel column containing 1 mL of NTA Ni Agarose (Qiagen). After repeated washing, the bound fraction was eluted with 250 mM imidazole (Fischer) in lysis buffer containing 10% glycerol (Acros).

SDS-PAGE and Agarose Gel Electrophoresis. SDS-PAGE gels were 15% w/v SDS-PAGE gels made in house with 37.5:1 acrylamide:bis (chemicals from Sigma). Samples were prepared with Laemmeli sample buffer, and loaded into BioRad mini-protean II electrophoresis system at 150 volts until dye ran to the end of the gel. Agarose gels were all 1.5% w/v agarose stained with ethidum bromide (Fischer) and imaged on BioRad GelDoc imager.

Bradford Assays. Bradford assay was either purchased from Pierce or made in house. Absorbances were routinely read 15 minutes after sample addition to G-250. Homogenates were 50 mg to 100 mg wet weight. Microspheres were 5 mg to 10 mg wet weight. Each data set included BSA standards, and all protein concentrations were generated by individual BSA standard curve.

Hydrogel Homogenate Production and Protein Binding. Hydrogels were made by adding 150 µL PEGDA (MW 575, Sigma Aldrich) to varying concentrations of glutathione (Sigma Aldrich, Alfa Aesar) and 0.05% w/v irgacure 2959 (Ciba). PBS was used to bring total volumes to 1 mL. The tubes were cured overnight under a UV light (purchased from a local hardware store, 0.25 $mW/cm^2$ 254 nm, measured on UVX radiometer). Gels were homogenized with a plastic homogenizer in the eppendorf tube and washed with 10 mL PBS in scintillation vials (at least 5 buffer changes over two days).

Microsphere Production. Microspheres were produced by a modified reverse emulsion polymerization method. Polymer solution contained 300 µL, PEGDA (d=1.1 g/mL, Sigma), 600 µL, PBS, 5 µL, eosin Y). Polymer solution (100 µL) was transferred to a glass test tube (1.5 mm diameter, 10 mm length) and 4 mL of mineral oil was added. The tube was vortexed 10 seconds until the polymer solution formed an emulsion in the oil. Ammonium persulfate (100 µL, 20%, Sigma) was added while vortexing, and vortexing continued for 1 min. Tetramethylethylenediamine (100 µL, 100%, TEMED, Acros) was added and vortexing continued for another minute. The tube was then left for 5 minutes until particles settled out, and several milliliters of deionized water were added. After most of the microspheres had settled into the aqueous phase (several minutes), oil was removed from the test tube and the solution containing the microspheres was collected in an eppendorf tube. The collected microspheres were then spun down, removed of their supernatant, and resuspended and washed with several changes of PBS, then washed over night in 5 mL PBS. Microspheres were compared to Glutathione Agarose purchased from Gold Biotechnology.

Microscopy. Brightfield and fluorescence microscopy was carried out on an Olympus IX70 inverted microscope.

Statistical Analysis. Statistical analysis was done using one tailed students t-test for pair wise comparison or ANOVA followed by post-hoc Tukey test for multiple sample comparisons. Significance was set at $\alpha$ less than or equal to 0.05. Each experiment was independently repeated three times and data is presented as mean plus or minus standard deviation unless otherwise noted.

Example 2

Creation of Vectors and Protein Expression

To create a model protein for purification, GFP was chosen for its solubility and ease of visualization. The vector, pET 15b (FIG. 1A), was constructed by inserting a flexible spacer sequence adjacent to the hexa-histidine tag and thrombin cleavable sequence and was confirmed by restriction mapping and subsequent sequencing (FIG. 1B, top). The sequence was isolated by PCR and cloned into pGEX 6p-1 adjacent to the GST sequence. This was confirmed by restriction mapping (FIG. 1B, bottom) and sequencing. GFP was isolated from gWIZ-GFP by PCR with primers that extended a separate spacer region and a second hexa-histidine tag. GFP was inserted into the pGEX vector for expression. The second hexa-histidine tag of the protein was not utilized in these experiments, but is relevant and must be noted because Ni-NT'A was used to purify the GST-GFP for several of the experiments being discussed. What effect on purification this may have was not analyzed. It is clear that these dual tags did not negatively impact the protein activity (fluorescence) or binding capability to GSH.

Resulting colonies were screened for gross fluorescence of the colonies (FIG. 1C, top), and sequencing. GST-GFP was readily observed (FIG. 1C, lower panel) and purified with a yield of approximately 300 mg/L of culture (data not shown). The purified protein fraction was run on a SDS-PAGE gel to confirm size and thrombin cleavability (FIG. 1D). The functionality of GST-GFP protein was confirmed by its increased affinity to nickel (data not shown) and glutathione beads, its green color and fluorescence, and its cleavability by thrombin. With the model protein produced and validated, the purification process was validated.

Example 3

Affinity of GST-GFP to Hydrogen Homogenates

Figure 2:
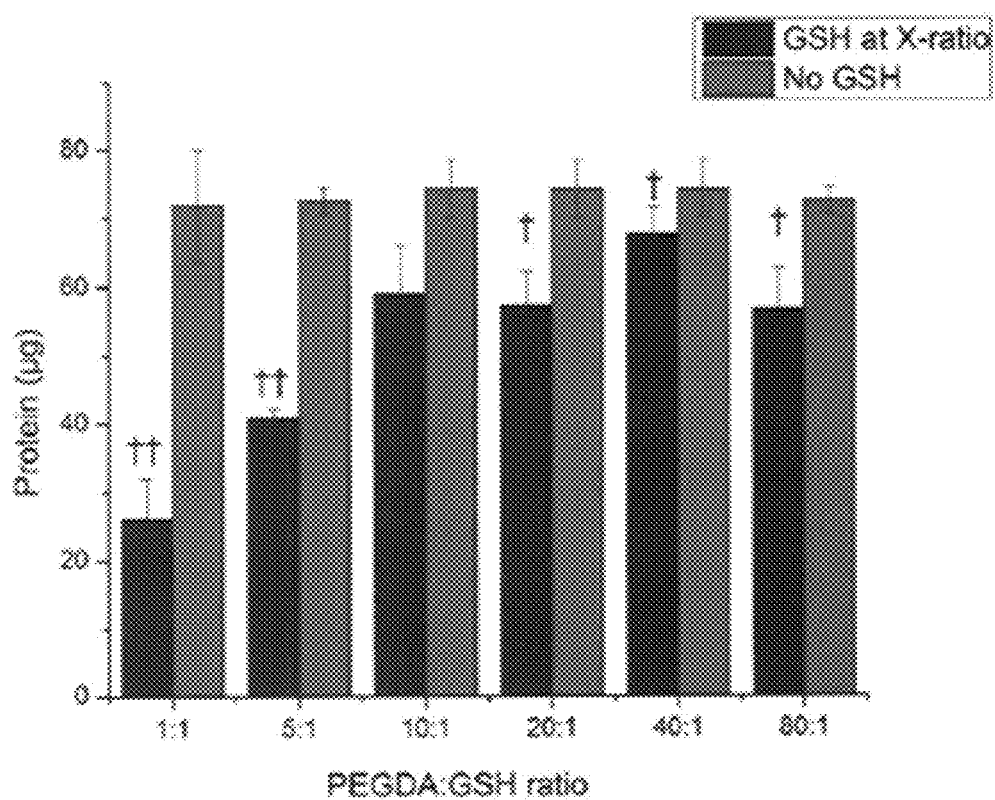
FIG. 2 shows affinity of GST-GFP to PEGDA:GSH homogenates. A: Influence of varying PEGDA:GSH (black) ratio to GSH alone (gray) as expressed by the amount (m) of protein in solution following 2 hour incubation. B: Influence of PEGDA:GSH ratios on bound, or incorporated, GST-GFP as expressed as percent GST. Total protein (100%) was 60 μg GST-GFP for all groups. + for p=0.05-0.01, ++ for p=0.01-0.001, +++ for p<0.001. Bars and points represent the mean of 3 independents samples plus or minus (±) standard deviation.
Figure 2:
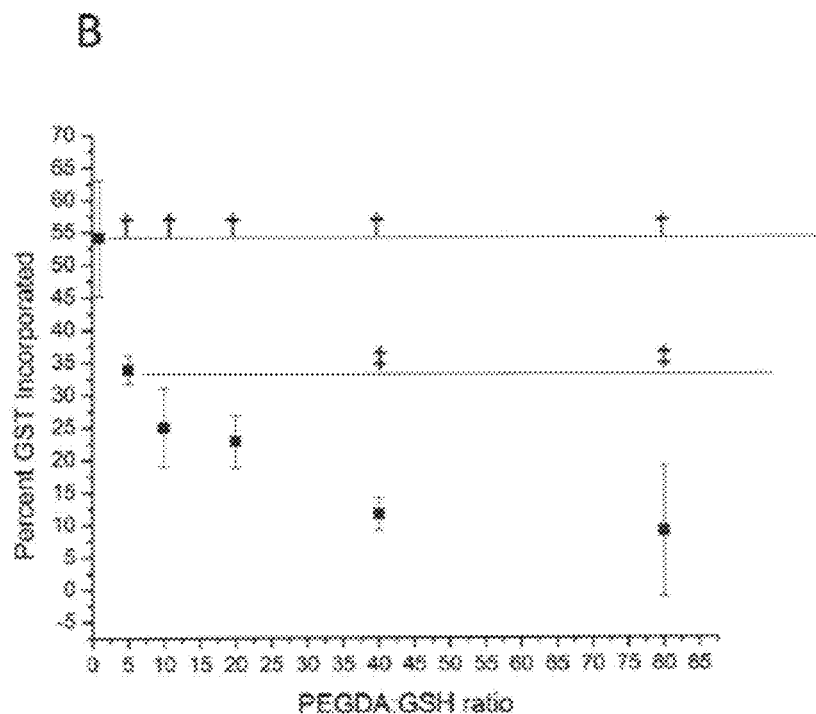

Hydrogels were made as described in Example 1 with varying PEGDA to GSH ratios, and the gels were homogenized, washed, and incubated with 60 µg of GST-GFP for 2 hours. When purified protein was incubated with the gels (FIG. 2), a significant decrease in GST-GFP was found in the solution after two hours compared to gel-free controls in the 1:1 ($p=0.008$), 5:1 ($p=0.005$), 20:1 ($p=0.02$), and 40:1 ($p=0.02$), 80:1 ($p=0.02$) PEGDA to glutathione ratio gels (FIG. 2A). There was clear increase in bound pre-purified (by 6xHis tag and nickel affinity columns) GST-GFP protein ($p=0.00002$), or decrease in free protein (FIG. 2B) when GSH was incorporated in the gels at the highest extent. The 1:1 and 5:1 ratio gels were statistically different from all other groups while the lower incorporation ratios did not associate with significantly differing amounts of GST-GFP. These experiments demonstrated significant protein association with gel homogenates harboring GSH compared to controls, and as the PEGDA:GSH ratio decreased, more GST-GFP was able to associate with the homogenized gels.

After homogenization and washing, PEGDA:GSH homogenates can be used to specifically purify GST tagged GFP. Further, we demonstrated that decreasing the PEGDA:GSH ratio from 80:1 to 1:1 resulted in increased GST affinity to gel homogenates. The PEGDA:GSH ratio was not further optimized because GSH inhibits polymerization reactions and gel formation at higher concentration. GSH is a known radical scavenger that decreases the number of free radicals available to sustain the polymerization cycle. GSH also incorporates into acrylate groups and stops chain growth by eliminating alkene groups necessary for polymer propagation. At some point, the PEGDA:GSH ratio would become low enough that no usable gel would form. Accordingly, gels that had qualitatively acceptable physical properties, i.e. handleability for homogenization, were focused upon.

Example 4

Specificity of GST-GFP to GSH Laden Hydrogel Homogenates

Figure 3:
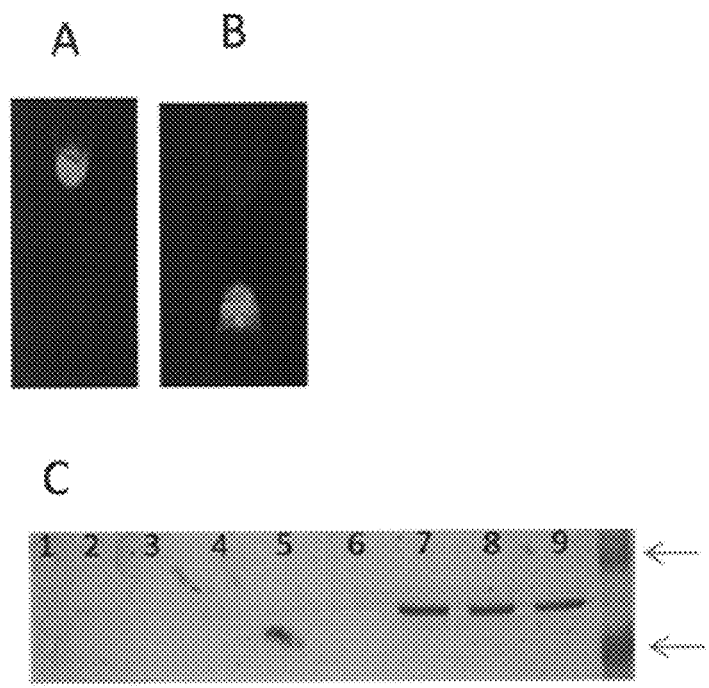
FIG. 3 shows elution and binding of PEGDA:GSH compared to PEGDA:Cys. A: Gross fluorescence observation of the gels confirmed GST-GFP association with homogenates prepared with PEGDA:GSH ratio (top) or PEGDA:Cys at the same PEGDA:Cys ratio (bottom). B: Gross fluorescence observation of the gels confirmed PEGDA:GSH homogenates eluted with either 10 mM cysteine (bottom) or 10 mM GSH (top). C: SDS PAGE electrophoresis confirmed that minimal protein eluted from (lanes 1-3) PEGDA gels eluted with GSH, (lanes 4-6) PEGDA:Cys gels eluted with GSH, but protein did elute (lanes 7-9) from PEGDA:GSH gels eluted with GSH. The last lane is a protein ladder, arrows indicating 100 kDa, and 55 kDa.

To confirm the specificity of the interaction, GST-GFP was incubated in the presence of homogenates made with equimolar GSH (FIG. 3A, top) or cysteine (FIG. 3A, bottom). There was no appreciable GFP observed in the cysteine-containing gels while the GSH-containing gels were visibly fluorescent. For homogenates made with glutathione, 10 mM GSH (FIG. 3B, top row) was able to elute the GFP completely while 10 mM cysteine (FIG. 3B, bottom row) was unable to elute the protein. Elution of the GST-GFP was found to be specific to GSH. No protein was eluted with GSH (lanes 1-3) from hydrogels lacking GSH incorporation or eluted by Cys (lanes 4-6) from gels including glutathione but proteins of appropriate molecular weight (FIG. 3C, lanes 7-9) were eluted with GSH from GSH-containing gels.

Example 5

Purifying GST-GFP from *E. coli* Protein Extract

Figure 4:
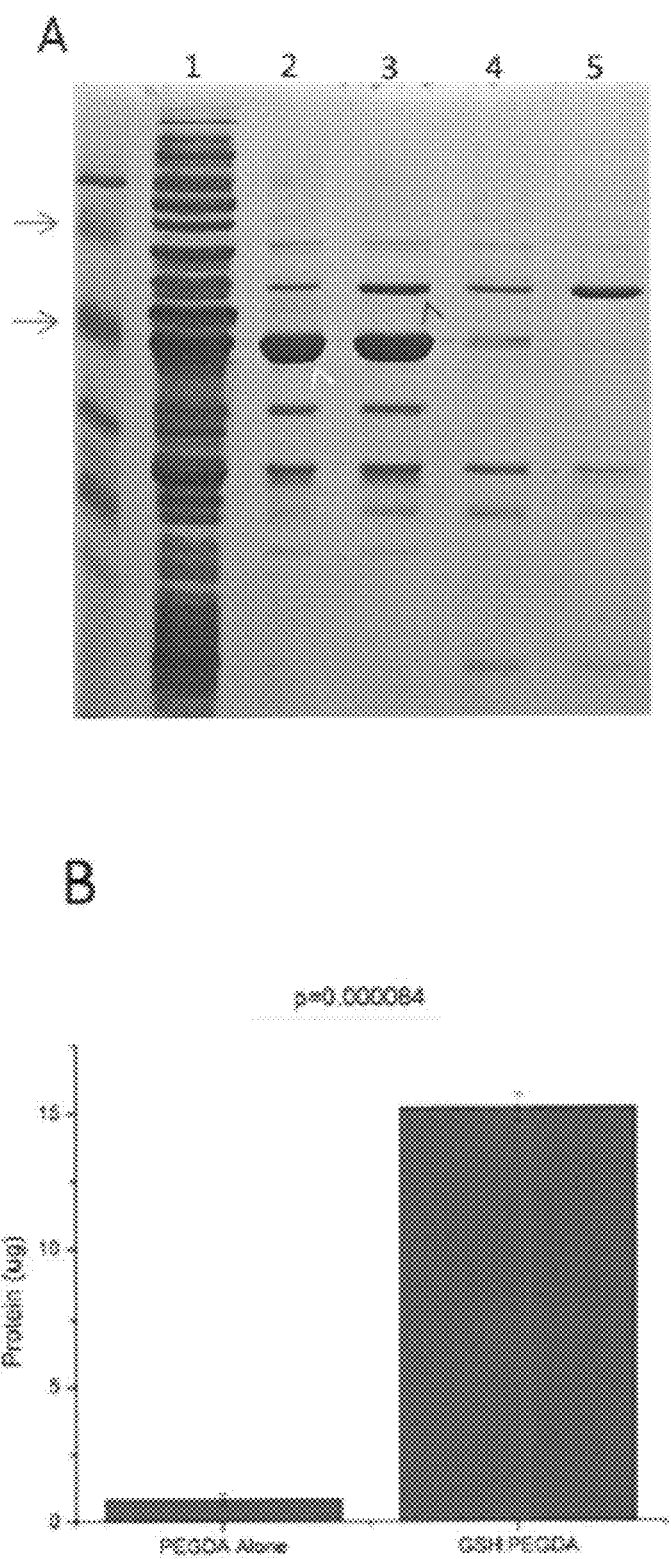
FIG. 4 shows SDS-PAGE of eluted and purified GST-GFP. A: SDS PAGE image of proteins obtained from (lane 1) crude soluble lysate, (lane 2) after Ni purification, (lane 3) Ni NTA purification in the presence of 10 mM glutathione, (lane 4) purification with PEGDA gel homogenate, and (lane 5) purified with PEGDA:GSH homogenate. Arrows indicate 100 kDa and 55 kDa. B: Relative protein recovered from PEGDA gel or PEGDA:GSH gel homogenates calibrated to total protein concentration from lanes 4 and 5 of panel. Data is presented as the mean plus or minus (±) standard deviation.

Although these experiments indicate that specific interactions take place between the gels and GST fusion proteins, this is not necessarily indicative of the ability of the materials to purify proteins from bacterial lysates. Using the homogenized 5:1 PEGDA:GSH gels, crude lysates including GST-GFP from the induced, soluble protein fraction was batch selected over 2 hours and eluted with 10 mM GSH. From soluble lysate, it was difficult to elucidate the GST-GFP protein (FIG. 4A, lane 1). Following nickel purification (FIG. 4A, lanes 2 and 3), the enriched fraction showed a high degree of purity and appropriate size as a monomer in absence of glutathione (lane 2), or as a dimer in the presence of glutathione (lane 3). Without GSH incorporation, little protein and no purification was achieved with PEGDA gels (FIG. 4A, lane 4). A significant single predominant band was obtained when purification took place in the presence of PEGDA:GSH gels (FIG. 4A, lane 5). The size of nickel purified GST-GFP eluted with imidazole (FIG. 4A, white arrow) is half the size of GST-GFP eluted with glutathione (FIG. 4A, black arrow). A protein of this mass was present in all samples and was twice the size of the GST monomer, which suggested dimerization. The absence of the GST monomer with excess GSH further suggested that the dimer would be the predominant protein present. It is known that the GST acts as a homodimer with its substrate between the two monomers. From 1 mL of the initial soluble GST-GSH lysate associated with the PEGDA:GSH homogenates, 0.8 µg were eluted from the PEGDA alone homogenates, and 15 µg were eluted from the PEGDA:GSH homogenate. This indicated an approximate 20 fold increased affinity of the GST-GFP to 5:1 PEGDA:GSH compared to PEGDA alone.

The homogenates were examined with fluoresence microscopy (FIG. 5A) and it was noted that the areas of fluorescence were of differing intensity that seemed to inversely correlate with the thickness of the homogenized piece. Further, there was expected variation between the size of the homogenized pieces that were between 10 µm and 500 µm (data not shown). Although the homogenization method may be acceptable for labs with the facilities to make the particles, these experiments allowed for optimization of the parameters necessary for protein purification, and therefore further improvements were possible. To improve the yield of purified protein and consistency of the purification process, it was hypothesized that more homogeneously distributed, smaller particles would allow for more efficient association of GST-GFP to the hydrogels.

Example 6

Creation of PEGDA:GSH Microspheres and Establishing Affinity to GST-GFP

Figure 5:
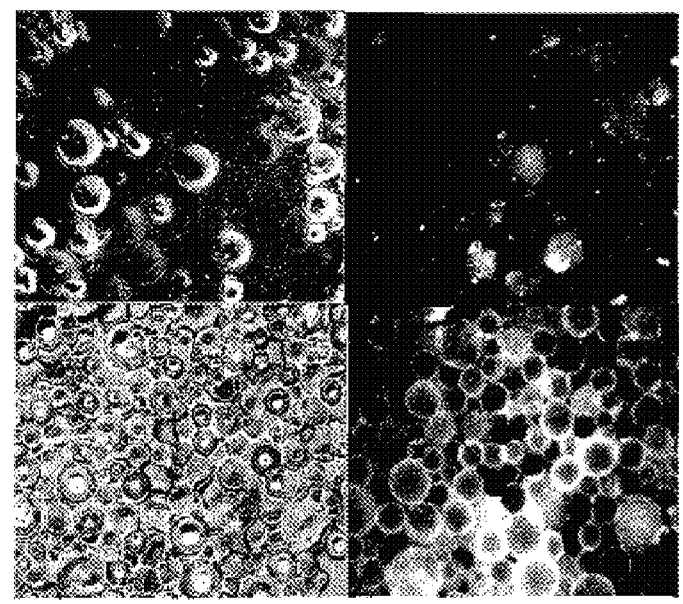
FIG. 5 shows microscopy of homogenates and beads, and comparison to GSH-agarose beads. A: Brightfield and epifluoresence microscopy of 5:1 homogenates made with PEGDA alone (top row), or a 5: I PEGDA:GSH molar ratio (bottom row). B: Brightfield and fluorescence microscopy of microspheres made with PEGDA alone (top row) and PEGDA:GSH (bottom row) at a 5:1 molar ratio. Scale bars represent 100 μm.
Figure 6:
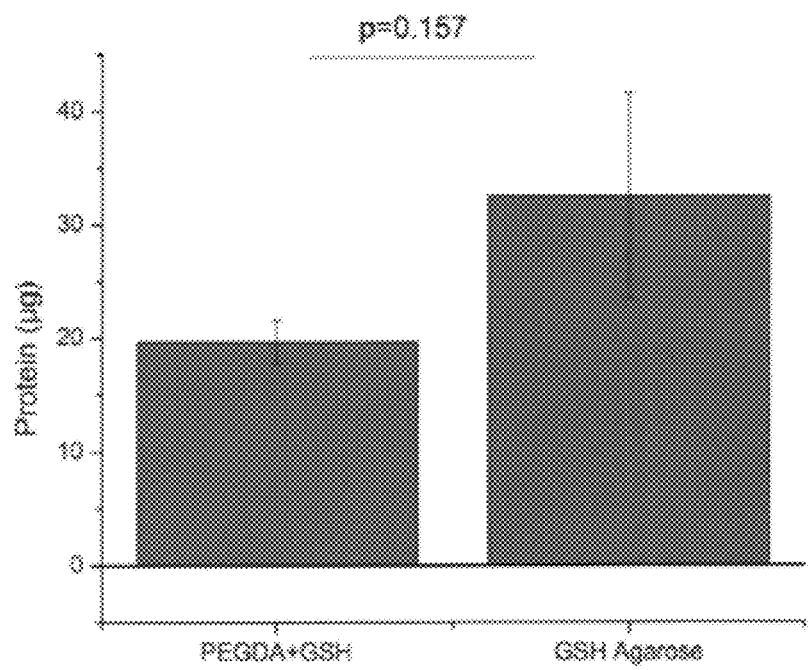
FIG. 6 shows GST-GFP association to PEGDA:GSH homogenates and PEGDA:GSH microspheres. Protein association comparison of GSH-agarose beads to 5:1 PEGDA:GSH microspheres. Data represent the mean plus or minus (+/−) SEM.

Microspheres were prepared using a reverse phase emulsion technique to obtain more control over size and shape of the particle. The spheres were more homogenously distributed between 10 µm and 200 µm spheres (FIG. 5). In addition, spheres made with 5:1 PEGDA:GSH showed significant and uniform association with the GST-GFP (FIG. 5B). Microspheres made from PEGDA:GSH had significantly greater affinity than PEGDA microspheres. In addition, there was no significant decreased in affinity to GST-GFP than purchased spheres made from GSH-agarose (p=0.157, one tailed student's t-test). It was hypothesized that homogenous sized, spherical microspheres would increase GST-GFP association with the hydrogels by increasing the surface area of the polymer available for protein association. Microspheres were produced with PEGDA:GSH ratios as low as 5:1, but yields decreased at lower ratios (data not shown). Spheres at a 5:1 PEGD:GSH molar ratio displayed significant interaction with GST-GFP over control gels without GSH. These easy to fabricate and inexpensive particles have great potential for protein purification, particularly since the microspheres interact similarly to purchased GSH-SEPHAROSE beads. Homogenates were able to remove 35% of the GST-GFP from the protein solution (FIG. 2B) while microspheres bind a similar amount of GST-GFP (FIG. 6) at 10 fold less mass. Simply put, microspheres demonstrated an increased binding capability compared to the homogenates. This increased binding may well be attributed to an increased surface area of the microspheres compared to homogenates, but further experiments would be needed to test this hypothesis.

Association of protein through the GST-GSH on PEGDA microspheres allows for therapeutic proteins to be released in the interstitial space either by enzyme cleavage by specific protease sites engineered between the GST and the therapeutic protein or by intracellular release by proteases, or high intracellular concentrations of reduced glutathione that would elute the GST from the glutathione-containing material.

Example 7

Materials and Methods for Examples 8

Figure 7:
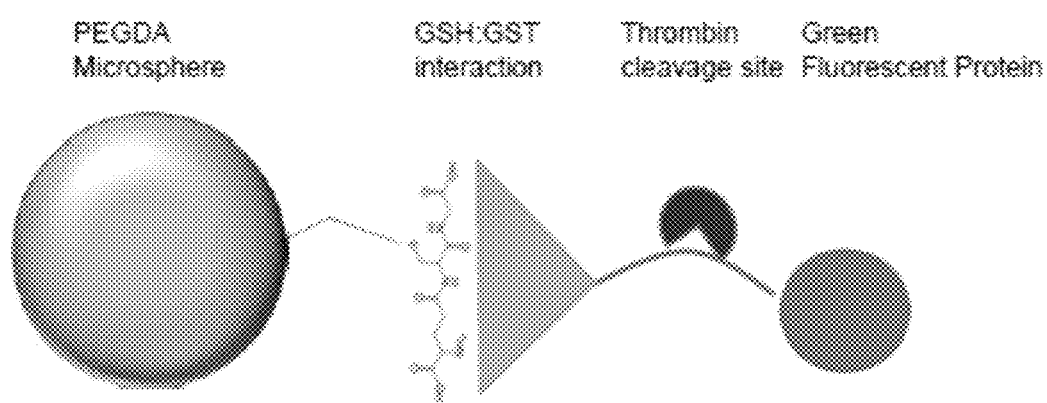
FIG. 7 is a schematic showing PEGDA microspheres have glutathione conjugated to them via thiol-ene addition during polymerization. The GST-GFP fusion protein anchors to this glutathione moiety. The thrombin site is designed to release the GFP from the fused GST and free the active protein from the microsphere.

Scheme. PEGDA microspheres having glutathione conjugated to them via thiol-ene addition during polymerization are shown schematically in FIG. 7. The GST-GFP fusion protein is anchored to the glutathione moiety. The thrombin site was designed to release the GFP from the fused GST and free the active protein from the microsphere.

Creation of GSH Laden Microspheres. Microspheres were created using a reverse-phase, emulsion polymerization method established in our laboratory. Briefly, reduced glutathione was mixed in a 1:5 molar ratio with 50% v/v PEGDA (Mr=575 g/mol). Two milliliters of mineral oil was added to 100 μL of the PEGDA: GSH mixture and vortexed. Resulting particles were washed over a week.

Mesh Size Measurements. Mesh sizes were calculated by extrapolating measurements of the swelling ratio of the polymer at relaxed and swollen states.

Particle Size Measurements and Microscopy. Images of GFP bound microspheres were acquired on an Olympus IX-70 inverted, fluorescence microscope. Images were captured on a Q-image Retiga 1300 CCD camera and measured by Q-image software.

Particle Counting. Particles were counted on a hemocytometer following trypan blue staining.

Gel Densitometry. SDS-PAGE gels were made in house and ran by standard protocols. Gels were imaged with a Sony Cybershot DSC-H9 on a light table illuminated by a standard fluorescent light bulb. Density of bands was measured after OD calibration with imageJ software.

Example 8

Size Distribution of PEGDA:GSH Spheres

We hypothesized that engineered, fusion proteins consisting of three parts: the first, a therapeutic molecule (modeled by the green fluorescent protein [GFP]), the second, an enzyme cleavage site serving as release mechanism for the therapeutic molecule (a thrombin site), and the third, a small molecule binding factor serving as an anchor for the system would be anchored in poly(ethylene glycol) diacrylate (PEGDA) microspheres until specifically released by cancer tissue (glutathione, [GSH]). PEGDA microspheres had an average diameter of 46 micrometers. Glutathione s-transferase (GST) tagged GFP was shown to specifically interact with the PEGDA:GSH sphere. Quantification of GST-GFP binding suggested the protein is coating the surface of the hydrogel with more than one layer. Hydrogel association of the GST-GFP did not affect thrombin cleavage of the GST from the GFP at the enzyme concentrations tested. Our results indicated that microspheres laden with GSH can effectively hold a GST tagged protein to their surface until released by external enzymes. Given low extra-cellular levels of GSH and higher thrombin activation in tumors, this interaction may prove promising as an anchor mechanism for protein therapeutics.

Figure 8A:
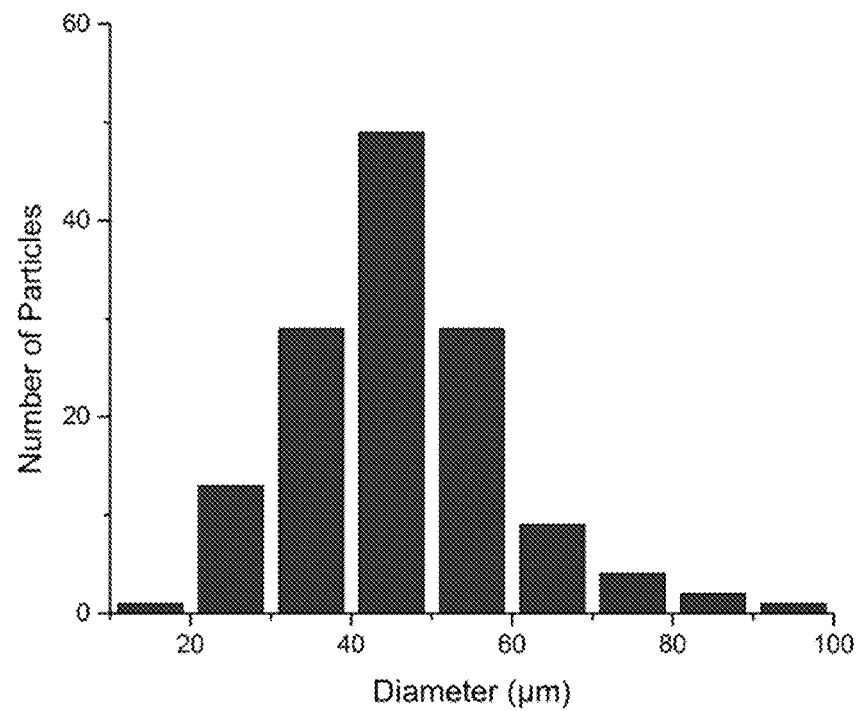
FIG. 8 shows size distribution of PEGDA microspheres as shown in a (A) histogram from measurements taken on (B) microscopic measurements of spheres. Brightfield (right), GFP fluorescence (middle), measured GFP fluorescence (right). Scale bar is 100 μm.
Figure 8B:
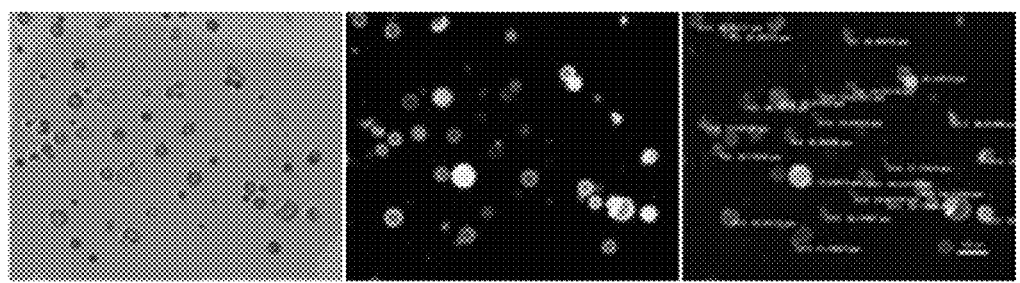
Figure 9A:
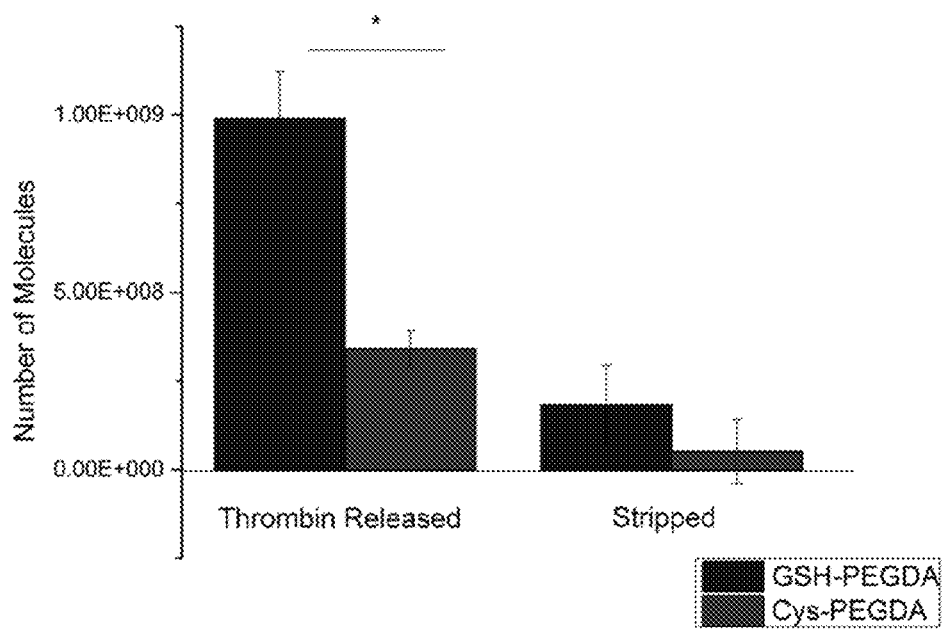
FIG. 9 shows after binding GST-GFP to PEGDA-GSH beads, beads were treated with excess thrombin for 3 hours at room temperature. (A) Beads were then boiled to remove all protein left protein fractions were quantified. (*p<0.05) (B) Varying the relative concentrations of thrombin with a fixed number of GST-GFP bound GSH spheres suggested a difference in thrombin Km. (C) This difference was verified upon repetition indicating GSH spheres act as inhibitors to thrombin cleavage (**p<0.05). (D) Brightfield and fluorescence images of PEGDA microspheres before (top row) and after (bottom row) thrombin treatment. After thrombin treatment, spheres lose GFP fluorescence. Scale bar is 100 μm.
Figure 9B:
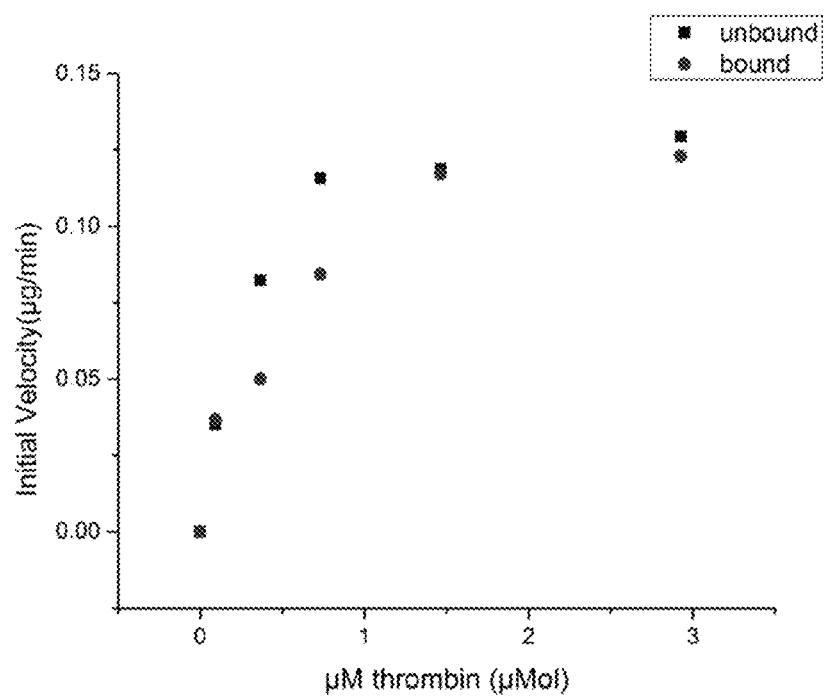
Figure 9C:
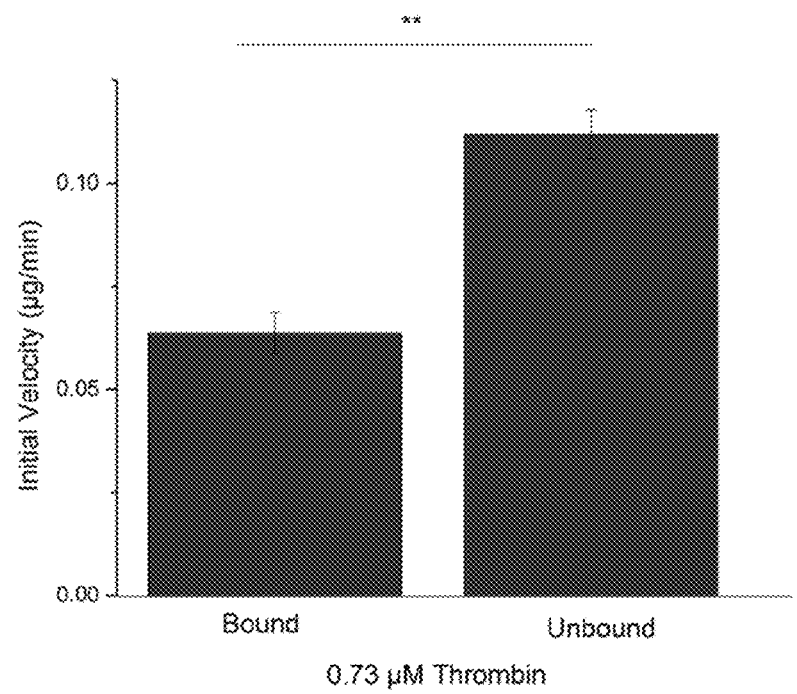
Figure 9D:
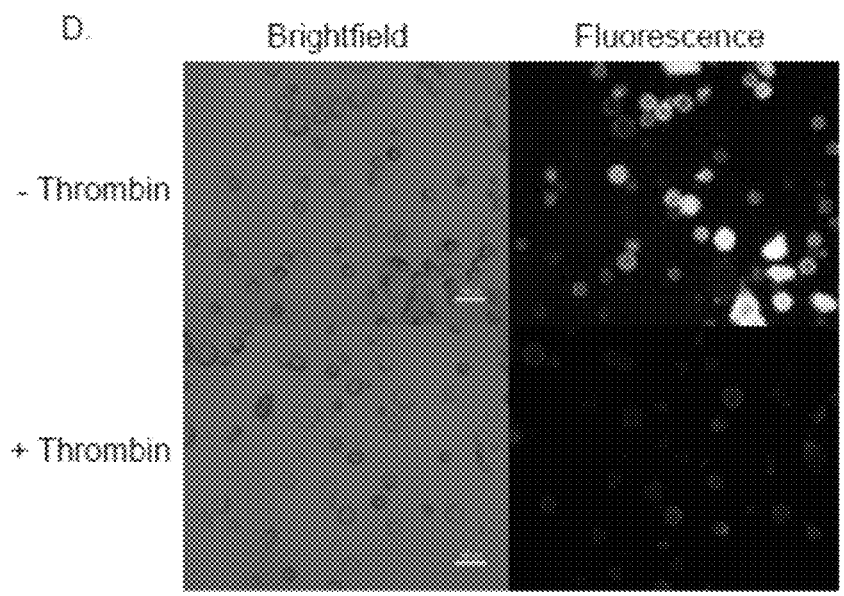

PEGDA microspheres were created with a diameter of 46±16 μm (FIGS. 8A and 8B, and Table 1.) The size distribution of the particles followed a normal distribution as measured by image analysis with GST-GFP bound spheres. GFP was bound to these spheres at a cleavable concentration of $9.9 \times 10^8$ molecules/particle (Table 1). This corresponded to a concentration of about 1 μg GST-GFP/10,000 PEGDA spheres. Protein was eluted from the spheres with 10 mM reduced glutathione and was cleaved from the particles with thrombin. Experiments with thrombin suggested that the Michaelis constant (Km) may be suppressed by binding to the PEGDA spheres, an observation that was subsequently confirmed. Mesh size measurements were made by swelling ratio analysis (data not shown) were found to be 4.6±0.237 nm. This was similar in size to the projected cross sectional area of the GFP.

TABLE 1

Parameters of PEGDA:GSH Microspheres.

| Parameter | Value (per sphere) |
| --- | --- |
| Diameter | 46 ± 16 μm |
| Surface Area | 7447 ± 6202 μm$^2$ |
| Mesh Size | 4.6 ± 0.237 nm |
| Release Capacity | $9.9 \times 10^8 \pm 2.5 \times 10^8$ molecules |

Extracellular glutathione levels have been shown to be 1000 times less than intracellular levels, which causes the extracellular environment to be an oxidative environment. The dissociation constant of glutathione from glutathione s-transferase has been measured to be 22 μM. This suggested that glutathione s-transferase would maintain a single glutathione in its binding pocket in the relatively glutathione-void extracellular environment.

Given the similarity in size of the cross-sectional diameter of the GFP alone (i.e., 4 nm), the mesh size of the hydrogel (i.e., 4.6 nm), the loading time of 3 hours, and the binding capacity, it was likely that GST-GFP association was predominantly on the surface of the PEGDA microspheres.

Nevertheless, an appreciable amount of protein was bound to the surface of these particles, indicating their potential for delivering therapeutic amounts of protein if they were implanted into a tumor. The protein was shown to be released by thrombin (FIG. 9), an enzyme that is unregulated in high grade astrocytomas. These characteristics made the GSH/GST interaction a promising, natural interaction in which to anchor protein therapeutics to delivery systems.

Example 9

Materials and Methods for Examples 10-14

Cloning of Melittin Gene into Expression Vector. Melittin was cloned using standard cloning procedures. All restriction enzymes were purchased from New England Biolabs, MA. The melittin peptide was GIGAVLKVLTTGLPAL-ISWIKRKRQ (SEQ ID NO:2). The rDNA was codon optimized by the JCAT codon optimization tool:

```
                                        (SEQ ID NO: 10)
AGC GGA TCC GGT ATC GGT GCT GTT CTG AAA

GTT CTG ACC ACC GGT CTG CCG GCT CTG ATC

TCT TGG ATC AAA CGT AAA CGT CAG TAG GAA

TTC TCA CG
```

Figure 10:
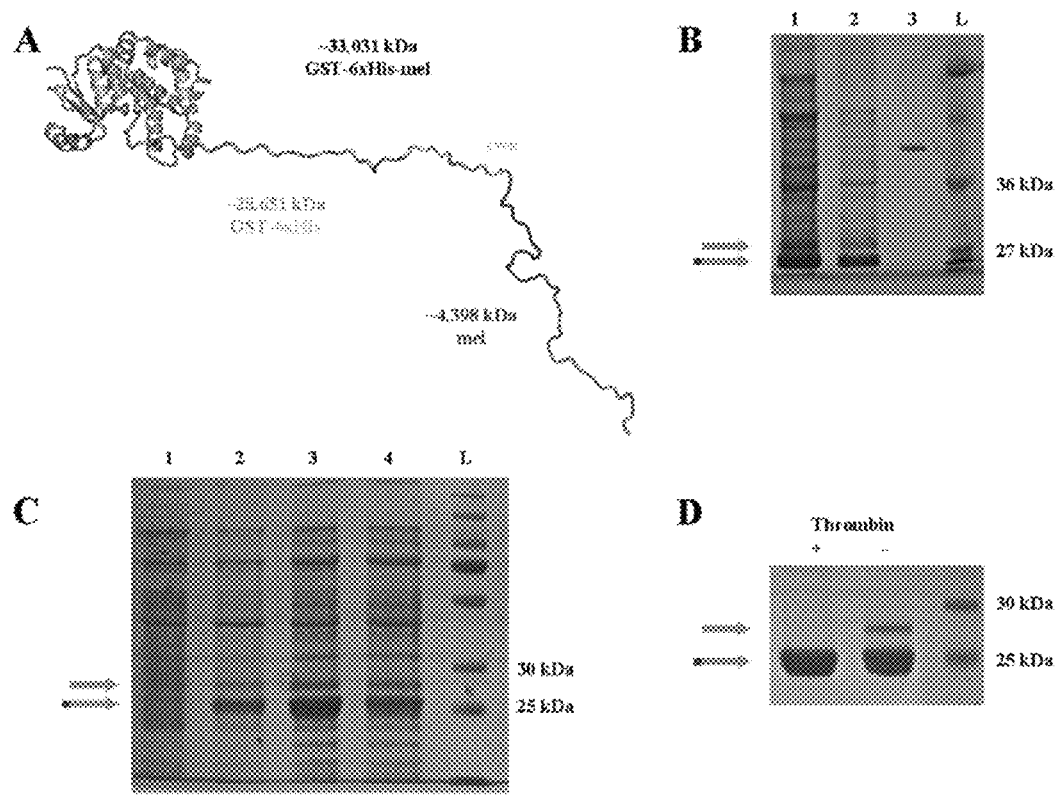
FIG. 10 shows purification of GST-6xHis-melittin from soluble protein fraction. (A) Predicted structure of GST-6xHis-melittin fusion protein based upon template matching. Approximate molecular weights are denoted below fragments as they would be generated by thrombin cleavage following the sequence LVPR (SEQ ID NO:1). (B) GST-6xHis-melittin was induced with 1 mM IPTG for 16 hours (lane 1) or 3 hours (lane 2) and compared with 200 ng of bovine serum albumin (BSA; lane 3), and a protein ladder for size (L). (C) GST-6xHis-melittin was also induced for 16 hours at 37° C. (lanes 1 and 2) or 25° C. (lanes 3 and 4) with 0.1 mM (lane 1 and 3) or 0.01 mM IPTG (lane 2 and 4). (D) The induced GST-6xHis-melittin has two purified products of the expected sizes for the fusion protein and GST-6xHis (−). Upon addition of 2 U thrombin (+), the GST-6xHis-meittin was cleaved and only the GST-6xHis band was observed. In each panel, the gray and black arrow indicates GST-6xHis-melittin and the gray arrow indicates GST-6xHis.

Restriction sites BamHI (double underlined) and EcoRI (underlined) were engineered to the 5' and 3' ends respectively, and an amber stop codon (TAG, italicized and underlined) was engineered at the 3' end. This double-stranded fragment was synthesized by Integrated DNA technologies (Skokie, Ill.) and was cloned into the pJB-HTS variant of the pGEX6p-1 expression vector (GE Healthcare Biosciences, Pittsburgh, Pa.), generating pJB-HTS-melittin. Positive clones were screened by direct sequencing (ACGT, Wheeling, Ill.). The layout of the expected protein is N-GST-6xHis-thrombin cleavage site-melittin-C, thus allowing dual purification with glutathione or nickel columns (FIG. 10A).

Expression and Purification of Melittin. GST-6xHis-melittin containing plasmid (pJB-HTS-melittin) was transformed into competent E. coli Rosetta 2 cells (Novagen, Darmstadt, Germany) in order to negate the truncating effects of underrepresented codons within restriction sites on the pJB-HTS vector, upstream of the melittin insertion (CTC, AGA, GGA) and to eliminate reduced expression effects of the outer membrane protease T and Lon protease. Cells from saturated, overnight starter cultures were incubated at 37 degrees Celsius at 180 revolutions per minute (RPM) until the desired cell density ($A_{600}$ about 0.4) before addition of IPTG, 0.1 M and 0.01 M, and removal to the appropriate induction temperature, 37° C., 25° C., or 4° C. After induction for varying times, for 3 or 16 hours, cells were collected by centrifugation at 3600 g and 4° C. for 20 minutes and was resuspended in lysis buffer (50 mM NaHPO4, 300 mM NaCl, 10 mM imidazole, buffered at pH=8.0). Lysozyme (1 mg, Sigma-Aldrich, St. Louis, Mo., L7651) was added to the resuspended bacteria, and the suspension was subjected to 3 rounds of freezing on dry ice and thawing in cold water. Samples were sonicated at 40% intensity (Misonix sonicator, model XL2015, Newtown, Conn.) three times for 15 seconds each followed by 15 seconds on ice, or until they were no longer viscous. The lysate (1 mL) was aliquoted to microcentrifuge (eppendorf) tubes and centrifuged for 30 minutes at 11,300 g and at 4° C. to pellet the insoluble fraction. The soluble fraction was removed, and the insoluble fraction was suspended in 500 µL of detergent-containing phosphate buffered saline (PBS). The buffer choice depended on the desired pH. A pH of 2.3 is designated as "low pH" and a pH of 7.4 is designated as "high pH." Low pH groups were attained by either the addition of 70 mM TCEP.HCl (+TCEP; Thermo Scientific, Hanover Park, Ill.) or 70 mM glycine (−TCEP) buffered at pH 2.3 to PBS. High pH groups were attained by adding 10 N sodium hydroxide to PBS with 70 mM TCEP.HCl until the pH was 7.4 or by using PBS alone. The fractions were then centrifuged at 11,300 g at 4° C. for ten minutes to re-pellet the remaining insoluble material. The detergent-containing soluble fraction was removed and analyzed by SDS-PAGE. GST-melittin containing fractions were further purified by Nickel-NTA agarose (Qiagen, Germantown, Md.) or agarose immobilized GSH (GoldBio, St. Louis, Mo.) affinity according to the manufacturer's recommendations and after raising the pH of the protein solution to approximately 7.5 with 1 M sodium hydroxide. Protein was eluted from beads in appropriate elution buffer recommended by the manufacturer but was also supplemented with 10% glycerol to increase protein stability during storage at −80° C. Total protein was determined by the Bradford Assay (Thermo Scientific, Hanover Park, Ill.) used according to the manufacturer recommendations and measured with a Beckman model DU640 spectrophotometer (Brea, Calif.). Recombinant melittin was purified as described, then digested with 2 units (U) of thrombin for 2 hours at 37° C. Protein molecular weights were confirmed with matrix-assisted laser desorption-ionization-time of flight (MALDI-TOF) mass spectroscopy (Applied Biosystems, Grand Island, N.Y.).

All SDS-PAGE gels were between 12% and 15% acrylamide crosslinked at a 1:37.5 ratio with N,N'-methylene bisacrylamide (Thermo Scientific, Hanover Park, Ill.). Samples were prepared in Laemmli buffer and boiled for one minute before loading. Gels were run in a Biorad (Hercules, Calif.) mini-protean II apparatus between 100 and 200 V. After completion of the run, gels were stained with Coomassie brilliant blue R-250 (Thermo Scientific, Hanover Park, Ill.) according to manufacturer recommendations.

Tumor Cell Growth Inhibition. All proteins were incubated with thrombin at 37° C. for two hours prior to cellular assays. Malignant glioma cells, U-87 MG, (ATCC, Manassas, Va., 3,000 cells/cm$^2$) were seeded in a 96 well plate together with appropriate treatments in 100 µL DMEM and 10% FCS (Sigma-Aldrich, St. Louis, Mo.). Treatments included a cell only control (untreated), thrombin (2 U), GST (10 µM), GST-6xHis-melittin (10 µM), GST-6xHis-melittin (10 µM) simultaneously with thrombin (2 U), or synthetic melittin (10 µM; GenScript RP20415, Sigma-Aldrich, St. Louis, Mo.). The cells with their respective treatments were incubated at 37° C. in 5% CO2 overnight, approximately 16 hours. The MTS assay (Promega, Madison, Wis., CellTitre96) was performed according to the manufacturer recommendation and incubated for two hours before reading absorbance at 495 nm on a Labsystems Multiskan plus plate reader (Thermo Scientific, Hanover Park, Ill.).

Bacterial Growth Inhibition. Following digestion with thrombin as described above, GSH-agarose beads (GoldBio, St. Louis, Mo.) were used to separate GST from recombinant melittin. Synthetic melittin and GST-6xHis-melittin underwent a similar process without thrombin or being subjected to GSH-agarose treatment. Overnight cultures of S. pyogenes (ATCC, Manassas, Va., BAA-1633) cells were diluted in chemically defined medium were diluted to approximately $10^8$ colony forming units (CFUs), corresponding to an absorbance at 600 nm ($A_{600}$) of 0.1, and 150 μL distributed into 96-well, optical-bottom plates (Greiner BioOne, Frickenhausen, Germany) for treatment. GST-6xHis-melittin, recombinant melittin, or synthetic melittin (10 μM) were then added and the plate was incubated at 37° C. with shaking using a Biotek Synergy 2 plate reader (Winooski, Vt.). Absorbance ($A_{600}$) measurements were obtained every ten minutes for 12 hours.

To measure growth of IPTG induced or non-induced E. coli, the bacteria was diluted to approximately $10^8$ colony forming units (CFUs) in LB medium, corresponding to an absorbance at 600 nm ($A_{600}$) of approximately 0.1, and 150 μL was distributed into 96-well, optical-bottom plates (Greiner BioOne, Frickenhausen, Germany). Antibiotics and IPTG were added to the appropriate groups, and the plate was incubated at 37° C. with shaking using a Biotek Synergy 2 plate reader (Winooski, Vt.). Absorbance ($A_{600}$) measurements were obtained every ten minutes for 12 hours. Growth curves were fit to the linear growth equation and compared by two-way ANOVA analysis.

Statistical Analysis. Purification conditions were examined one time, but subsequent density analysis on gels was done in triplicate and blinded in order to reduce bias. U-87 MG and S. pyogenes growth assays were repeated with three biological replicates. ANOVA followed by post-hoc Tukey tests were used to determine significance at $\alpha \leq 0.05$.

Example 10

Expression of Recombinant GST-6xHis-Melittin

The plasmid, pJB-HTS-melittin, was designed, cloned, and confirmed to express a fusion protein of GST followed by a hexa-histidine tag, a thrombin cleavage site, and the melittin fragment (FIG. 10A). Two variations of induction time, three hours and sixteen hours, were assessed for protein expression (FIG. 10B). Total protein and GST-6xHis-melittin (gray and black arrow) were produced at a greater level during the sixteen-hour induction compared with the three-hour induction. Therefore, all future expression studies used the sixteen-hour condition as the induction time.

To determine if the protein band at approximately 25 kDa could be diminished by induction under varying conditions, bacteria were induced at three temperatures, 37° C., 25° C., and 4° C. (4° C. data not shown), and 2 IPTG induction concentrations, 0.1 M and 0.01 M IPTG, to optimize the production of protein (FIG. 10C). Thrombin cleavage reduced the size of a 29 kDa band to 25 kDa, which correspond to the calculated sizes of GST-6xHis-melittin and GST-6xHis (FIG. 10D). The 0.1 M IPTG induction at 25° C. for 16 hours was the best of the conditions tested based solely on ratio of GST-6xHis-melittin to GST-6xHis from SDS gels; however, in all cases tested, greater than 90% of the dominantly expressed protein was GST-6xHis and not the GST-6xHis-melittin fusion protein. Based upon the clear identification that the predominantly expressed protein, when analyzed by mass spectrometry, was confirmed to have the predicted mass of GST-6xHis-melittin, we sought to improve the conditions for GST-6xHis-melittin induction and purification.

Example 11

Induction of GST-6xHis-Melittin

Figure 11:
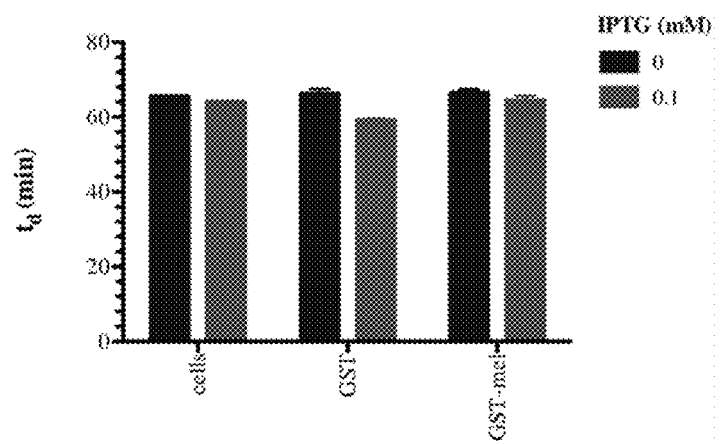
FIG. 11 shows doubling time ($t_d$) of *E. coli* and *E. coli* harboring GST-6xHis (GST) or GST-6xHis-Melittin (GST-mel) expression plasmid vectors. *E. coli* were grown under antibiotic selection to maintain expression vectors for GST-6xHis, GST-6xHis-melittin, or no expression vector control and were grown in the presence and absence of 0.1 mM IPTG. Doubling times were found to be dependent upon the plasmid and IPTG treatment (2-way ANOVA, p-value <0.05 for the interaction, [IPTG], and plasmid).

The optimization steps for IPTG concentration, induction time, and temperature were all executed using soluble GST-6xHis-melittin as a marker of efficiency (denoted as a black and gray arrow in figures). However, even at the most efficient condition, more than 90% of protein that was purified by nickel or GSH affinity chromatography did not contain active melittin fusion (FIGS. 10B and 10C, gray arrow). We hypothesized that the melittin fused to the C-terminal of GST-6xHis was being degraded or simply cleaved from the fusion protein. Melittin actively incorporates into membranes of cells as a multimeric protein, so we hypothesized that enriched GST-6xHis-melittin may be in association with the inner membrane of E. coli. We measured the rate of E. coli growth cultures with or without addition of IPTG to assess whether GST-6xHis-melittin affected E. coli growth. IPTG induction of other recombinant proteins in E. coli has been reported to have a minimal affect the logarithmic phase growth rate, which agrees with our observations. The produced fusion proteins do cause statistically significant, but biologically insignificant, growth rate inhibition of the E. coli (FIG. 11). The fact that there is not significant growth inhibition suggested that the GST-6xHis-melittin cannot form pores, i.e. there is no observable cell death or the protein is not soluble.

Example 12

Detergent Extraction from Insoluble Fraction

Figure 12:
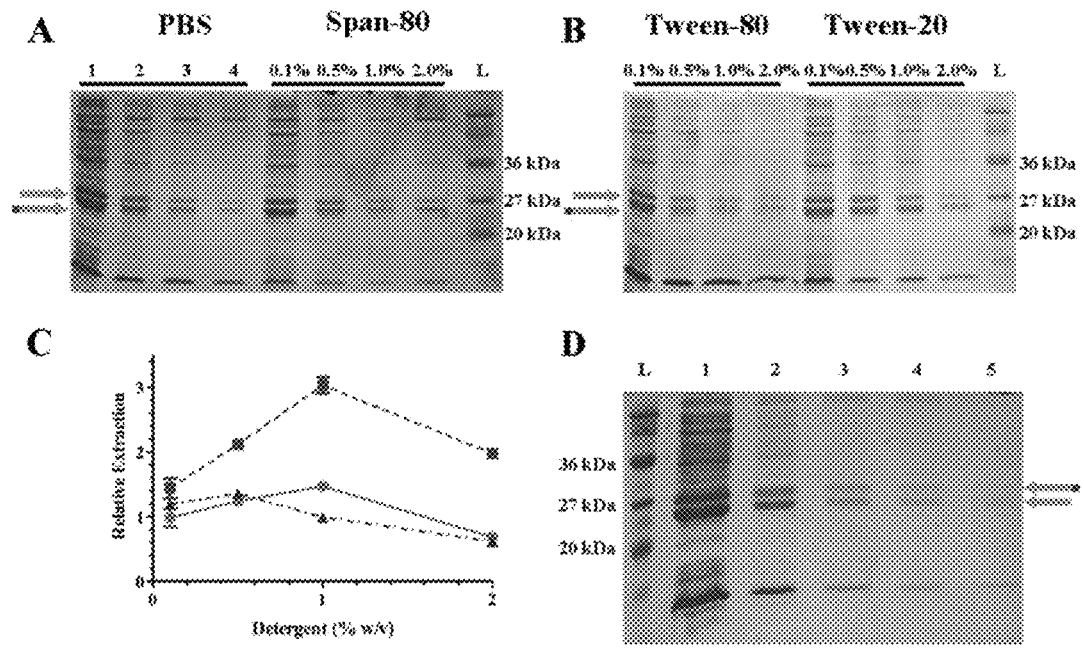
FIG. 12 shows extraction of GST-6xHis-melittin from the insoluble protein fraction. (A) Protein recovered from repeated extraction of the insoluble fraction with PBS (lanes 1-4 indicated the first through fourth PBS extraction) or sequential extraction with 0.1%, 0.5%, 1%, and 2% Span-80. (B) Protein recovered sequential extraction of the insoluble fraction with 0.1%, 0.5%, 1%, and 2% Tween-80 or Tween-20. (C) Semi-quantitative density of extracted GST-6xHis-melittin using Tween-80 (●), Tween-20 (■), or Span-80 (▲) relative to PBS extraction. Three technical replicates were examined and the mean plus or minus the standard deviation is presented. (D) Repeated extraction of same pellet using 1% Tween-20 where each lane indicates the number of extractions. The orange and magenta arrow indicates GST-6xHis-melittin and the orange arrow indicates GST-6xHis. A molecular weight ladder (L) is also included in each gel.

To extract what we believed to be a poorly soluble GST-6xHis-melittin protein, we compared extraction with buffer to 3 non-ionic detergents representing different hydrophilic-lipophilic balances (HLB):sorbitin monooleate 80 (HLB 4.3, Span-80), polysorbate 80 (HLB 15.0, Tween-80), polysorbate 20 (HLB 16.7, Tween-20) (FIGS. 12A and 12B). We chose non-ionic detergents because of their non-denaturing nature and capacity for removal by salt addition or by ion exchange chromatography. Interestingly, increasing HLB values (increasing hydropilicity) correlates with increased ability to purify melittin (FIG. 12B). PBS was able to extract melittin upon repeated exposure more effectively than Span-80 (FIG. 12A), but not as well as either Tween-20 or Tween-80 (FIG. 12B). It is remarkable how pure the GST-6xHis-melittin and GST-6xHis fractions became upon repeated extraction with either Tween-20 or Tween-80 without any further affinity purification. Repeated extraction with 1% Tween-20 was performed on the same insoluble pellet in order to maximize yield (FIG. 12C). Most of the extractable protein was removed after the first extraction. Nearly 50% of the GST-6xHis protein extracted from the insoluble fraction contained a melittin fusion, while the other 50% did not. These conditions resulted in the purification of soluble melittin of approximately 0.5 to 1 mg/L of E. coli culture. In comparison, we were able to achieve a pure melittin yield of less than 0.1 mg/L of E. coli from the soluble protein fraction, and less than 10% of what we purified from the soluble fraction contained an active melittin fusion.

Example 13

Acidic Solubilization of GST-6xHis-Mel

Figure 13:
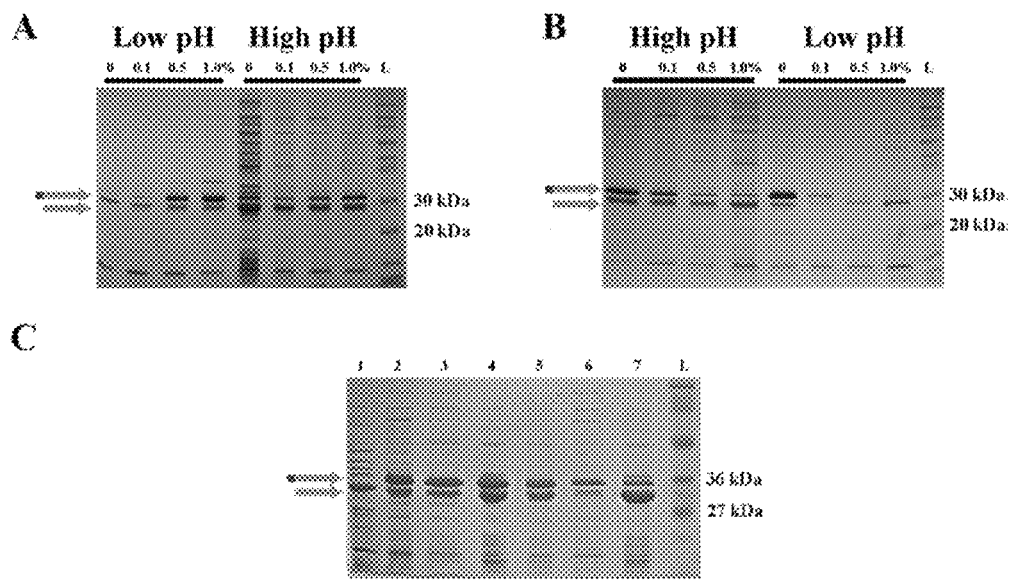
FIG. 13 shows acidic solubilization of GST during detergent extraction. (A) Sequential extraction of the insoluble protein fraction in the presence of TCEP and 0%, 0.1%, 0.5%, and 1.0% Tween-20 in PBS adjusted to pH 2.3 (low pH) or 7.4 (high pH). (B) Sequential extraction of the insoluble protein fraction in the presence 0%, 0.1%, 0.5%, and 1.0% Tween-20 in PBS adjusted to pH 2.3 (low pH) or 7.4 (high pH) in the absence of TCEP. (C) Extraction and nickel purification of GST-6xHis-melittin from 500 mL E. coli induction. The pellet was treated with acidic (pH of 2.3) buffer with no detergent (lane 1) followed by a first (lane 2) and second (lane 3) extraction of the pellet with 1% Tween-20 at a pH of 2.3 and eluted Ni-purified protein from the first (lane 4) and second (lane 5) extractions, respectively. The flow through from this nickel purification is also included (lane 6). Thrombin cleaved, nickel-purified protein from lane 4 (lane 7) shows a marked decrease in GST-6xHis-melittin band. The gray and black arrow indicates GST-6xHis-melittin and the gray arrow indicates GST-6xHis. A molecular weight ladder (L) is also included in each gel.

The isoelectric point of GST is known to be between 5.8 and 6.8, depending upon the specific sequence and was estimated to be 6.31 using a web-based calculation. The isoelectric point of melittin is considerably higher with an estimated pI of 12.01 for the recombinant, thrombin cleaved product. The predicted isoelectric point of a GST-6xHis-melittin fusion by primary sequence prediction is 8.2. We hypothesized that detergent extraction of the insoluble lysate at low pH would extract GST-6xHis-melittin by selectively solubilizing the more charged molecule. Further, because GST is known to form aggregates by disulfide bonding between four cysteine residues exposed on the surface, we sought to reduce these disulfide bonds using reducing agents. Extraction in the presence (FIG. 13A) or absence (FIG. 13B) of the reducing agent TCEP at low pH resulted in the selective purification of GST-6xHis-melittin. Interestingly, at lower detergent concentrations and at low pH, little to no GST-6xHis-melittin was extracted. As the detergent concentration exceeded 0.5%, selective extraction of GST-6xHis-melittin was achieved regardless of whether a reducing agent was present (FIG. 13). Likewise, at high pH, the reducing agent made little difference (FIG. 13) allowing us to conclude that the selective solubilization of GST-6xHis-melittin was not due to a simple process of reduction GST-inclusions.

The insoluble pellet from 500 mL of induced culture was extracted with low pH buffer without detergent (FIG. 13C, lane 1) then extracted twice with low pH buffer containing 1% Tween-20 (FIG. 13C, lanes 2 & 3). To remove the detergent from the GST-6xHis-melittin, the extract was purified by nickel affinity chromatography (FIG. 13C, lanes 4 and 5). Unexpectedly, a re-enrichment of the GST-6xHis degradation product occurred through this process. In fact, the purest GST-6xHis-melittin was found in the flow-through fraction of this process (FIG. 13C, lane 6). We digested GST-6xHis-melittin purified by metal affinity chromatography with thrombin to further verify that the product was, in fact, GST-6xHis-melittin (FIG. 13C, lane 7). The loss of the 37 kDa band and increase in intensity of the 29 kDa band suggested that the band was GST-6xHis-melittin.

GST has long been known to act as a homodimer. GST dimers occur only between members of the same GST class. Even in fusion proteins, this quaternary structure is maintained. Three possible combinations of dimers from GST-6xHis and GST-6xHis-melittin are possible: two homodimers consisting of either GST-6xHis:GST-6xHis or GST-6xHis-melittin: GST-6xHis-melittin, and one heterodimer consisting of GST-6xHis:GST-6xHis-melittin. GST-6xHis:GST-6xHis homodimers were thought to be diminished by acid solubilization; so only the homodimer of GST-6xHis-melittin:GST-6xHis-melittin, and the heterodimer of GST-6xHis:GST-6xHis-melittin were thought to remain. Melittin is a highly basic peptide and when engineered with a hexa-histadine tag, the melittin peptide may change the electrostatic interactions of the hexa-histadine sufficiently to disrupt formation of complexes between histidine and nickel. If this was the case, homodimeric GST-6xHis-melittin:GST-6xHis-melittin may have reduced affinity for nickel (FIG. 13C, lane 6), while what is retained on the resin would consist of heterodimeric GST-6xHis:GST-6xHis-melittin (FIG. 13C, lanes 4 & 5).

Example 14

Figure 14:
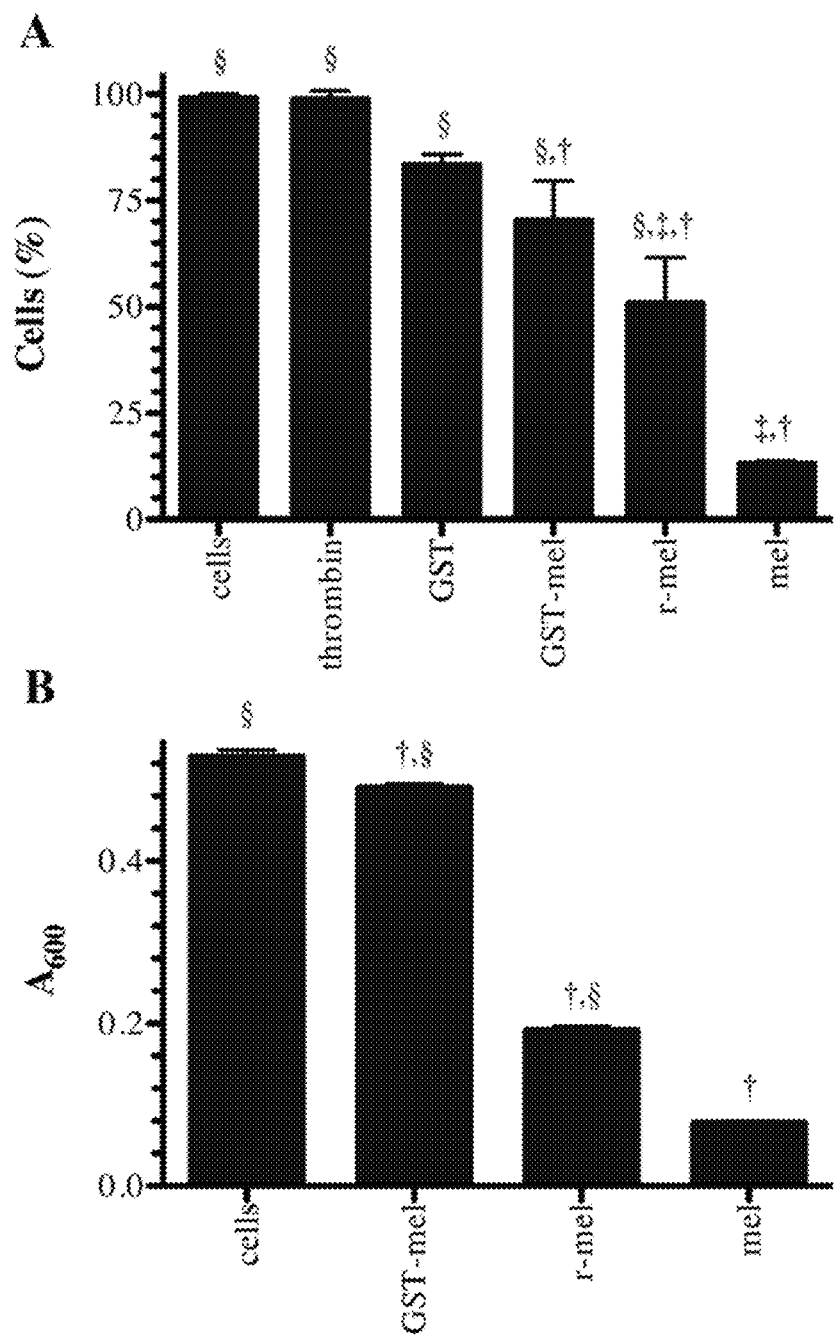
FIG. 14 shows functional characterization of recombinant melittin to synthetic melittin. (A) Survival of U-87 MG cells 3 hours after no treatment (cells), treatment with 2 U of thrombin (thrombin), 20 µM synthetic melittin (mel), recombinant GST-6xHis-melittin fusion (GST-mel), recombinant purified melittin (r-mel), or GST-6xHis (GST). (B) Growth, as measured by the absorbance at 600 nm, of S. pyogenes cells (cells) five hours after treatment with 10 µM recombinant melittin (r-mel), synthetic melittin (mel), or recombinant GST-6xHis-melittin (GST-mel). In each, three biologic replicates were examined and the mean plus or minus the standard deviation is presented. The symbols indicate significant difference (p-value less than 0.05) from the cells without treatment (†), treatment with GST (‡), or treatment with synthetic melittin (§).

Growth Inhibition Effect of Recombinant Melittin on U-87 MB and S. pyogenes To verify the activity of nickel-purified, recombinant melittin, the effects of 10 μM recombinant GST-6xHis-melittin and synthetic melittin were compared on U-87 MG cells (FIG. 14A). As controls, the effects of thrombin, and GST-6xHis were also considered in this experiment. Under these conditions at least 85% survival was observed in the GST-6xHis and thrombin treatment groups (FIG. 14A). Cells treated with GST-6xHis-melittin without thrombin retained 70% survival, whereas thrombin-treated GST-6xHis-melittin let to 50% cellular survival. Under similar conditions and concentrations, synthetic melittin allowed 15% survival of U-87 MG cells.

We further examined the potential of nickel-purified, recombinant melittin to inhibit growth of the Gram-positive bacterium, S. pyogenes. GST-6xHis-melittin fusion protein (10 μM), purified recombinant melittin (10 μM), or synthetic melittin (10 μM) were incubated with S. pyogenes cells. Synthetic and recombinant melittin almost completely inhibited the growth of S. pyogenes at 5 hours. GST-6xHis-melittin, however, exhibited minimal growth inhibition, similar to no treatment (FIG. 14B).

Accordingly, an unusual process for the purification of a GST-6xHis-melittin recombinant protein may be accomplished by repeated extraction of the insoluble protein fraction with detergent. High levels of purification were achieved simply by detergent extraction at a low pH. Usable quantities of functional melittin were purified by this method.

Example 15

Materials and Methods for Examples 16 and 17

Expression and Purification of Recombinant Proteins. Proteins were expressed and purified by standard methods. In brief, GFP was cloned from the pWiz-GFP plasmid (Aldevron) into the pGex-6p-1 plasmid (GE healthcare) by primer extension PCR. A hexa-histidine tag and thrombin cleavage site (LVPRGS) was added to the N-terminal of GFP prior to insertion, generating pJB-HTS-GFP. Melittin (GIGAVLKVLTTGLPALISWIKRKRQ (SEQ ID NO:2)) was codon optimized using JCAT: (AGC GGA TCC GGT ATC GGT GCT GTT CTG AAA GTT CTG ACC ACC GGT CTG CCG GCT CTG ATC TCT TGG ATC AAA CGT AAA CGT CAG TAG GAA TTC TCA CG (SEQ ID NO:10)) and cloned into the same vector replacing GFP after removal by BamHI and EcoRI generating pJB-HTS-melittin.

Proteins were expressed in BL21 (Novagen) and Rosetta (Novagen) Escherichia coli cells for GST-GFP and GST-melittin, respectively. In both cases, bacterial cells were grown to an absorbance at 600 nm ($A_{600}$) of 0.4 at 37° C. before 0.1 mM IPTG was added to induce protein production. Cells were removed to 25° C. and incubated for 16 hours to produce the fusion proteins. Bacterial cells were centrifuged before re-suspension in lysis buffer (50 mM NaHPO$_4$, 300 mM NaCl, buffered to a pH of 8.0). Cells were lysed by three freeze-thaw cycles on dry ice and 4° C. before three 15-second sonication (Misonix model XL2015) rounds at 40% intensity with 15-second incubation on ice between sonication rounds. The lysate was centrifuged at 12,000 RPM and 4° C. for 30 minutes to pellet the insoluble material. GST-GFP was predominantly in the soluble fraction and was purified by Ni-NTA chromatography (Qiagen) according to the manufacturer's recommendation. GST-melittin was predominantly in the insoluble fraction and was extracted by 1% Tween-20. The extract was then purified by Ni-NTA chromatography yielding a column elution product determined to be approximately 50% GST, 50% GST-melittin.

PEGDA Microsphere Formation, Protein Loading, and Characterization. PEGDA microsphere were created through a modified process of reverse phase emulsion polymerization. PEGDA (300 μL; MW=575 g/mol, Sigma)

was diluted in 300 µL PBS containing 30 mg reduced glutathione (GSH; Alfa Aesar) or 12 mg (equimolar with GSH) reduced cysteine (Sigma). Mineral oil (2 mL) was added to a borosilicate culture tube (1.5 mm diameter, 10 mm length). Monomer solution (100 µL) was added to the culture tube while vortexing for 10 seconds at full speed. While still vortexing, 100 µL of 20% ammonium persulfate (in PBS) was added followed by 50 µL N,N,N',N'-tetramethyl ethylene diamine. The mixture was vortexed for an additional minute. After that time, deionized water (2 mL) was added prior to centrifugation at 4° C., 4,000 rpm for 1 minute to recover the microspheres. Microspheres were washed over the course of a week with at least 10-fold volume excess of PBS and with 5 to 10 changes of PBS per day. Microspheres were loaded over the course of 3 hours with 50 to 100 µg of protein in PBS. Loading occurred on a rotator wheel, with gentle rotation at 20 RPM. After loading, microspheres were washed one time with 10-fold volume excess of PBS.

Microscopy was carried out on an Olympus IX70 inverted microscope with an epi-fluorescence illuminator. Images were captured by a Q-imaging Retiga 1300 CCD and analyzed on Q-capture suite. The diameter of at least 130 particles was measured from at least three different particle preparations for each formulation. Fluorescent images are pseudocolor micrographs using the fluorescent properties of GFP (excitation and emission: 488 and 519 nm) or trypan blue (excitation and emission: 595 and 660 nm). To determine particle density in solution PEGDA microspheres were counted using hemocytometer after staining with trypan blue (1% in PBS).

Mesh size of macroscopic hydrogels formed using identical conditions without emulsification were measured. Briefly, after polymerization in a 8 mm×2 mm cylindrical mold, polymers were suspended in 1-butanol and the mass of butanol displaced by the suspended polymer was noted. Hydrogels were swollen over twenty-four hours in deionized water, and their masses recorded. The hydrogels were returned to water and masses recorded at three-hour intervals until there was a difference between subsequent masses of less than 5%. At this point, the point of equilibrium swelling, the swollen hydrogels were resuspended in butanol and the mass of butanol displaced by the suspended polymer was determined. Hydrogels were then freeze-dried for 24 hours, and their dry weight recorded. Mesh size were estimated based upon the Flory-Rehner swelling theory.

Protein Identity, Quantitation, and Kinetics. Total protein was determined by the Bradford Assay (Pierce) according to the manufacturer recommendations and measured with a Beckman model DU640 spectrophotometer. Acrylamide gels were prepared in house by conventional protocols. All gels were between 12% and 15% acrylamide and cross-linked at a ratio of 37.5 to 1 acrylamide to bis-acrylamide. Gels were stained by Coomassie brilliant blue. Images were captured on a light table with a Sony DSC-H9 cybershot CCD.

Reaction kinetics were measured by semi-quantitative densitometry of SDS-PAGE gels. Reactions with equivalent concentrations of GST-GFP substrate and varying concentrations of thrombin (0.1, 0.33, 0.75, 1.5, and 3 µM) were incubated at 37° C. for varying amounts of time. In groups where cleavage from microspheres was reported, approximately 10,000 microspheres were used. Reactions were stopped by addition of Laemmli sample buffer (containing SDS) and stored at 4° C. until run on SDS-PAGE. All gels were run with known concentrations of BSA standards. Density measurements were made with NIH imageJ software with gel backgrounds normalized. Each thrombin concentration was run one time, except for 0.73 µM, which was ran in biological triplicate.

Protein Release. GSH mediated release studies were carried out over 6 days. Protein release was measured from 10,000 to 20,000 microspheres into 500 µL PBS in the presence and absence of glutathione. Release was measured with three independent replicates per experimental group. Preliminary studies (not shown) indicated that in this system, 50% of reduced glutathione becomes oxidized within 24 hours. Therefore, at each 24-hour time point, glutathione containing buffers were completely replaced. The buffer that was removed was frozen for later analysis. At the completion of the experiment, all frozen samples were thawed and 50 µL of each samples were diluted in PBS and read on a Quantech fluorometer.

S. pyogenes Growth Inhibition. In a volume of 100 µL, two-million PEGDA-GSH microspheres were loaded with GST-melittin over a period of three hours. The microspheres were washed with 10 times volume of PBS one time, and divided into two tubes. Thrombin (2 U) was added to one tube containing one-million GST-melittin loaded microspheres, and two additional units of thrombin were loaded to a third tube containing one-million GST-PEGDA microspheres that were not loaded with GST-melittin. Samples were incubated at 37° C. for two hours before the supernatant was removed.

Overnight cultures of S. pyogenes cells were suspended in chemically defined media and diluted to $10^8$ colony forming units in 150 µL. A portion of the supernatant (50 µL) was added to 96-well optical bottom plates (Greiner BioOne) along with a 150 µL aliquot of S. pyogenes cells. This plate was incubated at 37° C. for twelve hours. At ten-minute intervals, the absorbance (Biotek Synergy 2 spectrophotometer; Winooski, Vt.) at a wavelength of 600 nm (A600) was recorded.

Statistical Analysis. ANOVA was used to test all groups, and post-hoc Tukey analysis was utilized for pairwise comparison if ANOVA suggested significant differences between the groups. In all cases a less than or equal to 0.05 was considered significant.

Example 16

Binding and Release of GST-GFP to PEGDA Microspheres

Figure 15A:
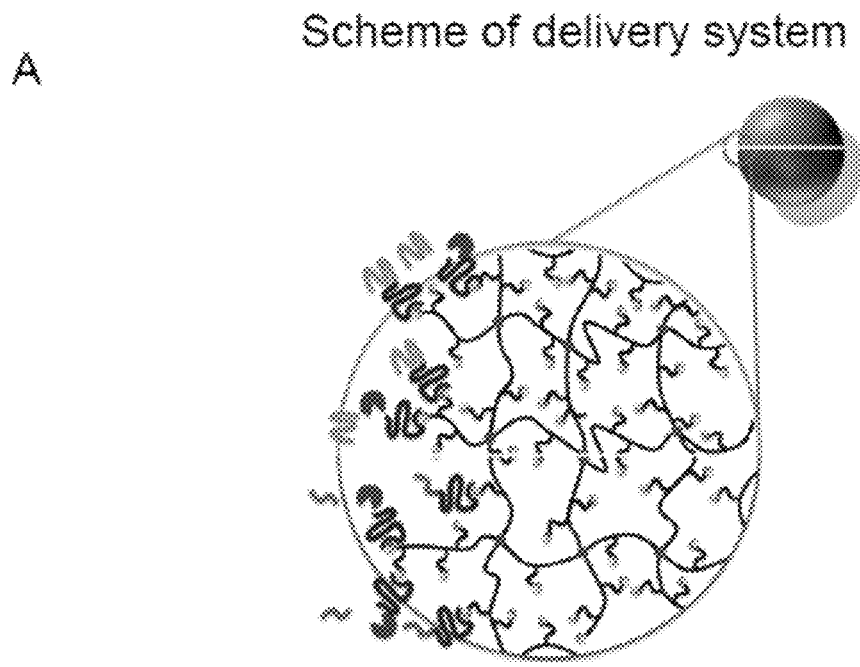
FIG. 15 shows schematic of PEGDA-GSH microspheres and predicted structure of GST-GFP and GST-melittin. (A) Schematic showing half of a GST-GFP (green) and half of a GST-melittin (orange) microsphere with a magnified region of the microspheres suggesting the surface and internal structure. In the magnified region, black entanglements indicate the crosslinked (grey circles) PEGDA mesh with pendant glutathione (GSH; gold spheres). GST (blue)-GFP (green) and GST-melittin (pink) fusion protein are shown binding to GSH. Thrombin (brown) is shown cleaving melittin or GFP from GST fusion partners by acting on a thrombin cleavage site in linker fragment (shown as red line). (B) Predicted structures of of GST-GFP fusion protein and GST-melittin fusion protein dimers used to predict the size of the fusion proteins.
Figure 15B:
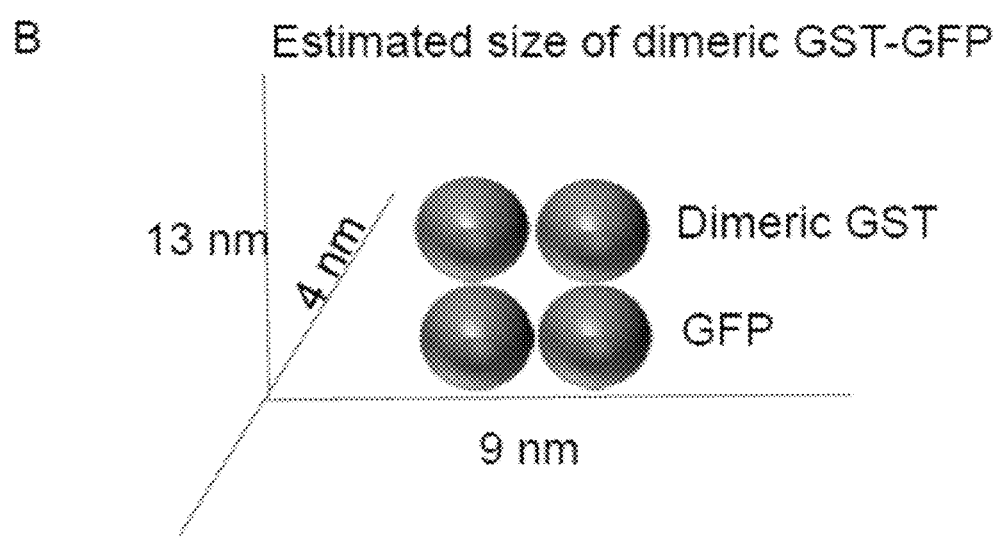
Figure 16A:
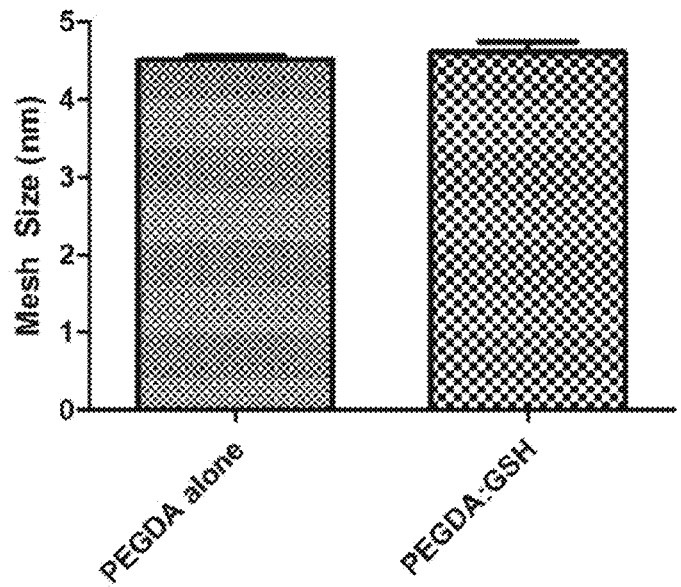
FIG. 16 shows physical characteristics of PEGDA-GSH microspheres. (A) Mesh size of microspheres was calculated to be 4.5 nm (p>0.05) in both PEGDA and PEGDA-GSH microspheres. Each bar represents the mean plus or minus the standard deviation of three independent samples. (B) Representative histogram of diameters of PEGDA-GSH microspheres from a single production. Three batches were used to calculate average microsphere diameter. (C) Brightfield and pseudocolored green fluorescent micrograph of PEGDA-GSH microspheres associated with GST-GFP.
Figure 17A:
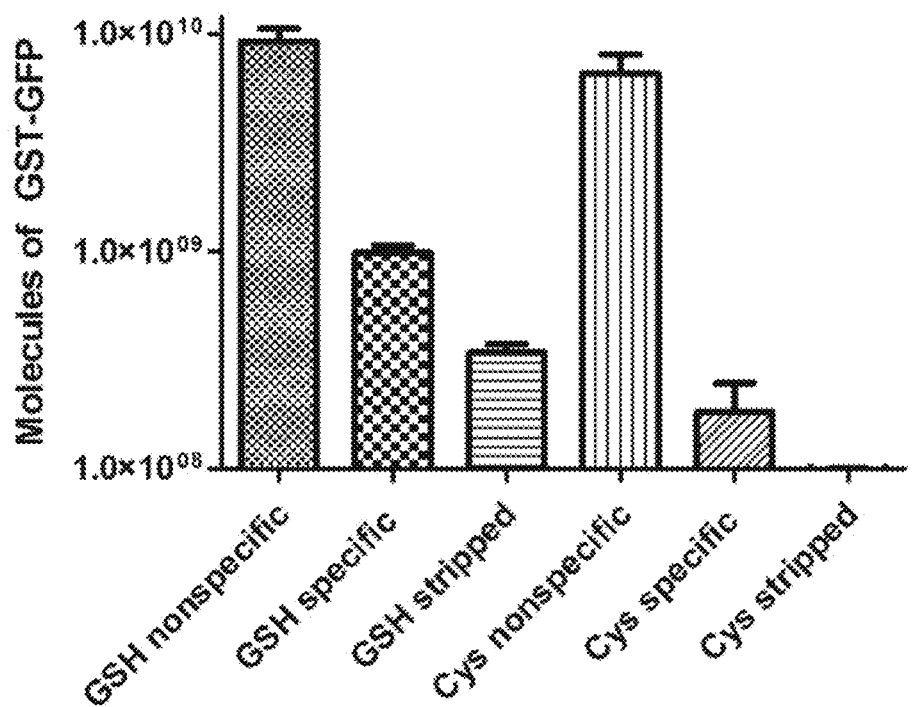
FIG. 17 shows binding of GST-GFP to PEGDA:GSH microspheres. (A) GST-GFP binding to microspheres. Non-specific, specific, and stripped GST-GFP measured associated with Cys-PEGDA or GSH-PEGDA hydrogel microspheres. Each bar represents the mean plus or minus the standard deviation of three independent samples. (B) Pseudocolor micrograph of GST-GFP (green) bound to GST-PEGDA microspheres counterstained with trypan blue (red). The scale bar is 10 µm.
Figure 17B:
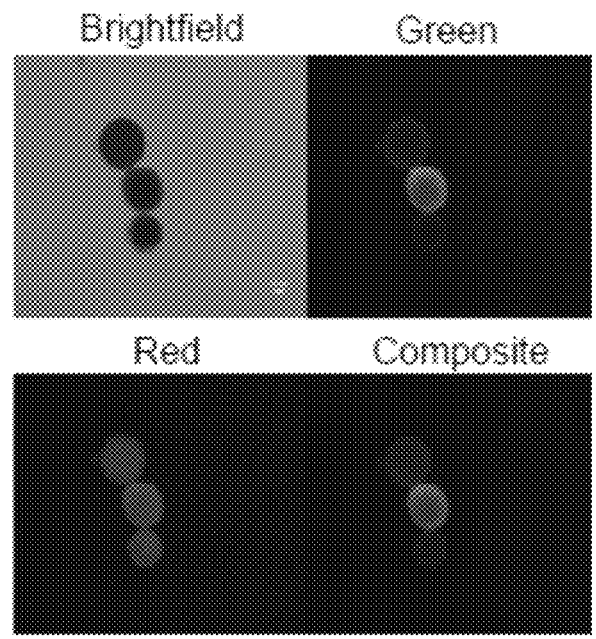

GST is known to have approximate dimensions of 9 nm by 9 nm by 5 nm in its dimeric form, the native state of GST in solution. We reasoned that the even larger GST-GFP fusion; the GST-GFP fusion dimer was estimated to be 13 nm×9 nm×6 nm based upon measurements of GFP and structure predictions (FIG. 15B). Knowing this, we measured the mesh size ($\xi$) of the hydrogel, and found a mesh size ($\xi$) of approximately 4.5 nm. The addition of 5 to 1 molar ratio of PEGDA to GSH did not significantly affect mesh size (FIG. 16A). Based upon estimates of fusion protein size and the mesh size, GST dimers would be unlikely to enter the hydrogel mesh even without a fusion partner present. To further support this, PEGDA-GSH microspheres were loaded with GST-GFP and stained trypan blue to allow the location of the protein to be determined. Microspheres illuminated with epifluorescent microscopy exhibited GFP, i.e. green fluorescence, predominantly on the surface of microspheres and trypan blue, i.e. red emission, diffusely throughout the microspheres (FIG. 17B). Accordingly, the interaction between GST-GFP and PEGDA-GSH microspheres was occurring predominantly at surface of the microspheres.

Figure 16B:
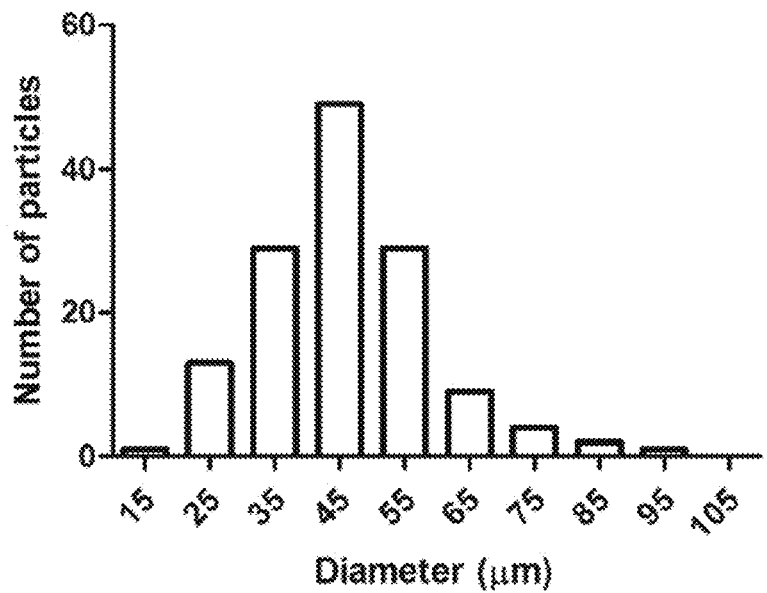
Figure 16C:
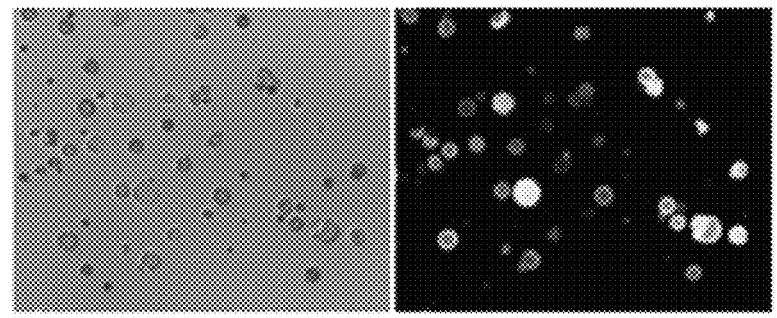

Assuming that the entire surface of a PEGDA microsphere was available for interaction with GST-GFP, we calculated the number of GST-GFP that could bind to the surface assuming perfect, monolayer coverage. Hydrogel microspheres had an average diameter of 46±16 μm (FIG. 16B, Table 2) resulting in an average surface area of 7447±6202 μm² (Table 2) after synthesis, washing, and loading with GST-GFP. Measurements on control PEGDA-cysteine (cys) microspheres showed similar size and surface area distributions (FIG. 16B). Assuming an ellipsoid shape of the dimeric GST-GFP (FIG. 15B), we reasoned that the average cross sectional area of a GST-GFP molecule to be $2.8 \times 10^{-5}$ μm² (FIG. 15B). Given these values and the assumption that all GST-GFP loading is on the surface, we predicted that monolayer coverage of an average PEGDA-GSH microsphere would consist of $2.6 \times 10^8$ molecules of GST-GFP.

TABLE 2

Summary of Physical Characteristics of PEGDA:GSH Microspheres.

| | Parameter | Calculated Value | Observed Value |
|---|---|---|---|
| Particle | Diameter (μm) | N/A | 46 ± 16 |
| | Surface Area (μm²) | N/A | 7447 ± 6202 |
| | Mesh Size (nm) | N/A | 4.6 ± 0.2 |
| GST-GFP | Cross Sectional Area† (μm²) | $2.8 \times 10^{-5}$ | N/A |
| | Capacity§‡ (molecules) | $2.6 \times 10^8$ | $9.9 \pm 2.5 \times 10^8$ |

With the estimate of the amount of protein loaded on the microspheres, the ability to release the protein in a specific manner was assessed. PEGDA-GSH and PEGDA-cys microspheres were first loaded for three hours with GST-GFP. Microspheres were then washed with PBS to remove protein that was loosely bound or any protein that was transferred with the loosely associated water phase. The microspheres were treated with thrombin. The resulting cleavage products were run on a gel and quantified with gel densitometry. Thrombin was able to cleave $9.9 \pm 2.5 \times 10^8$ molecules of GFP from a PEGDA-GSH microspheres. Based upon this result, GST-GFP bound to PEGDA-GSH microspheres represents significantly more than a monolayer coverage, while PEGDA-Cys microspheres released approximately ten-fold less.

Figure 18:
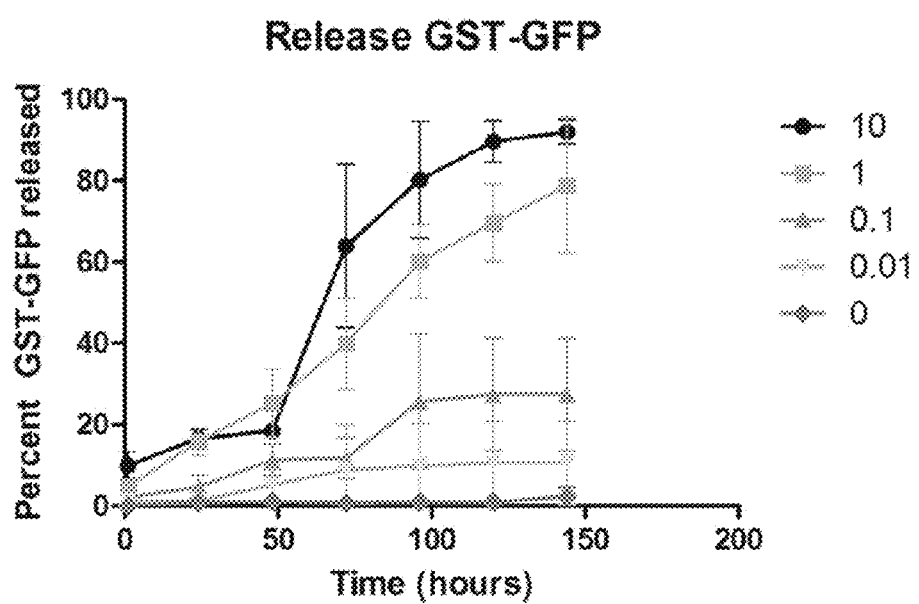
FIG. 18 shows release of GST-GFP. Release of GST-GFP in the presence of 10 mM (●), 1 mM (■), 0.1 mM (▲), 0.01 mM (▼), and 0 mM (♦) GSH containing phosphate buffered saline. Each point represents the mean plus or minus the standard deviation of three independent samples.

To further confirm the specificity of the interactions of GST-GFP with the surface and to understand the response of the microspheres to injection into extracellular fluids, we examined the release of protein from microspheres in the presence of GSH. GSH is available at low levels (0.1 mM) in extracellular compartments of the body. Extracellular GSH will elute proteins immobilized by GST/GSH interactions, but based upon the knowledge of the association constant, $K_m$, between GSH and GST ($2.2 \times 10^{-2}$ mM), the elution of GST-GFP protein anchored to PEGDA-GSH microspheres was expected to be low. Over a period of time, GST-GFP elution was measured in buffer containing various GSH concentrations. GSH at intracellular levels (10 mM, and 1 mM) significantly eluted GST-GFP within 48 hours. Extracellular levels of GSH, i.e. concentrations below 1 mM GSH had a much less prominent disruption of the microsphere GST-GFP interaction with more than 80% of the protein remaining associate with the particles after 6 days (FIG. 18).

Figure 19A:
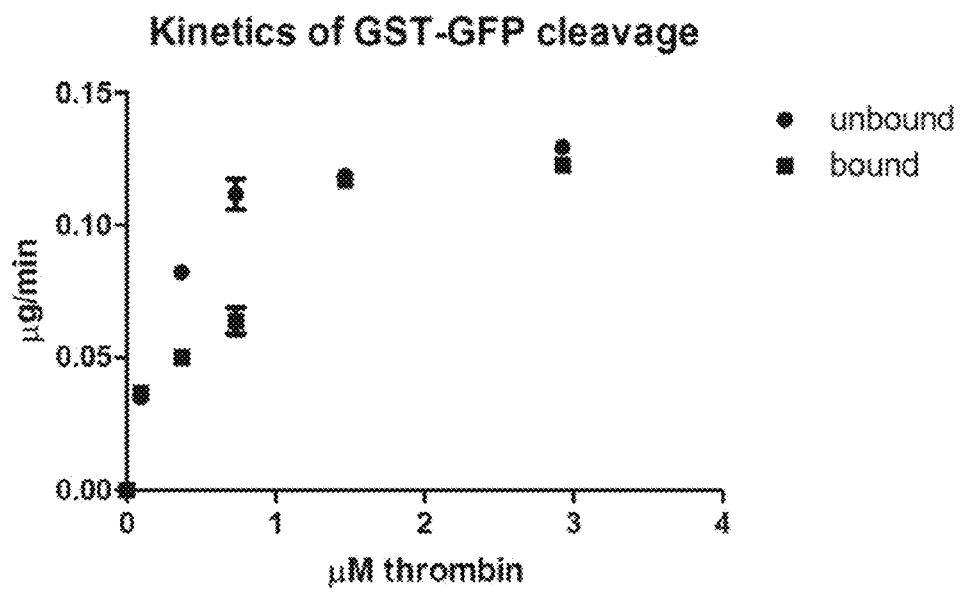
FIG. 19 shows kinetics of thrombin cleavage of GST-GFP free, and in association with PEGDA microspheres. (A) Michaelis-Menten curve showing apparent $V_{max}$ for both bound and unbound GST-GFP is similar but $K_m$ was increased when GST-GFP is associated with PEGDA-GSH microspheres. (B) Representative brightfield and epifluorescent micrographs depicting GST-GFP (green) associated with microspheres before (top row) or after (bottom row) release in response to thrombin (2 U).
Figure 19B:
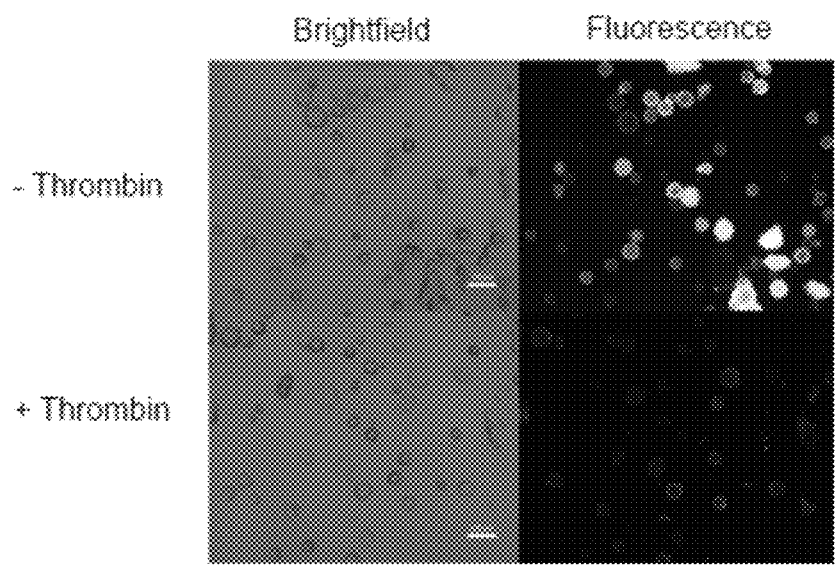

With an understanding that the association is specific, it was sought to determine the release in the presence of physiologic proteases that could release the therapeutic protein. To understand the rate of release in response to activating protease, the Michaelis-Menten parameters for thrombin cleavage were measured for GST-GFP in association with the PEGDA-GSH microspheres and free GST-GFP (FIG. 19A). Compared with the absence of thrombin (FIG. 18), significantly faster GFP release was observed when thrombin mediates the release. Protein was released in minutes compared days when no enzymatic response was present. By comparing the rate of GST-GFP cleavage between free GST-GFP and PEGDA-GSH associated GST-GFP, we found that the Michaelis-Menten constant (Km) of thrombin to GST-GFP was significantly increased from approximately 0.18 μM to 0.30 μM when GST-GFP was in association with PEGDA-GSH microspheres (FIG. 19A). It was also clear that the GFP is released from PEGDA-GSH microspheres after thrombin exposure (FIG. 19B).

Example 17

GST-Melittin Loaded Microspheres Inhibit Growth of *S. pyogenes*

Figure 20A:
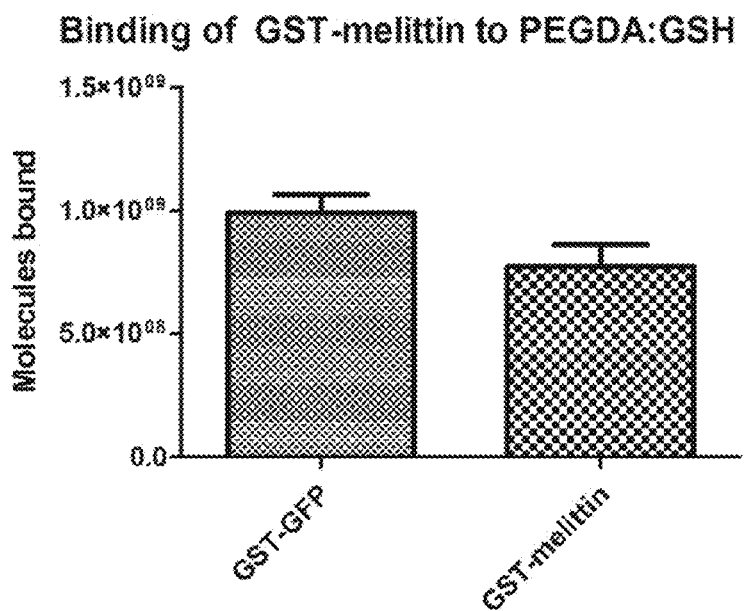
FIG. 20 shows GST-melittin microspheres inhibit growth of S. pyogenes. (A) Binding of GST-GFP and GST-melittin to PEGDA microspheres. (B) Growth inhibition of S. pyogenes cells exposed to defined growth media, defined growth media with melittin, or defined growth media mixed with the releasate from PEGDA-GSH microspheres with thrombin, PEGDA-GSH microspheres bound with GST-melittin, or PEGDA-GSH microspheres bound with GST-melittin and exposed to thrombin (2 U). Each bar represents the mean plus or minus the standard deviation of three independent samples.
Figure 20B:
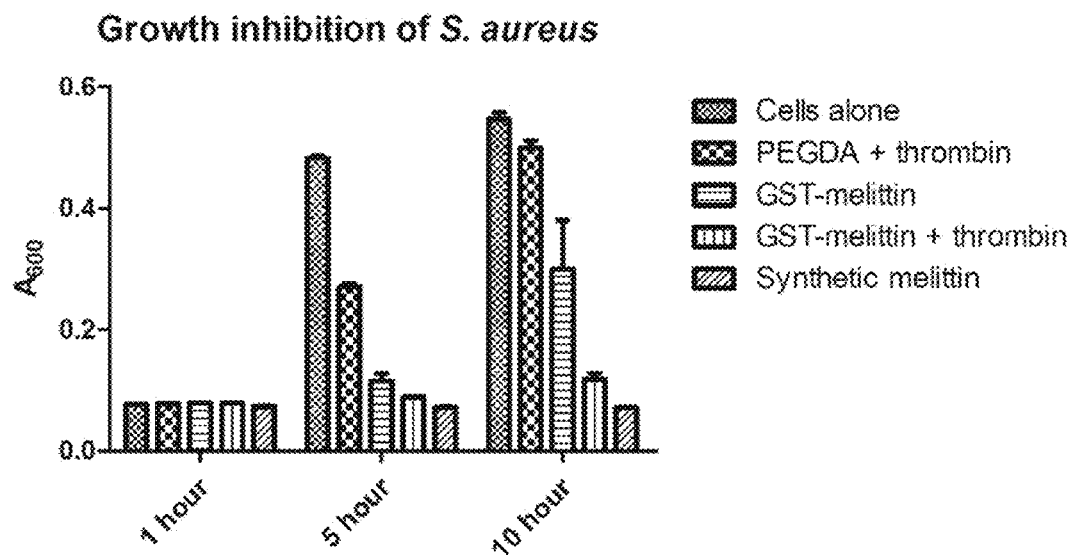

To determine the effectiveness of the GSH-GST interaction as a thrombin mediated, anti-bacterial coating, GST-melittin was generated and loaded onto PEGDA-GSH microspheres in a manner equivalent to the GST-GFP protein. After confirming that GST-melittin binds to PEGDA-GSH microspheres similarly to GST-GFP (FIG. 20A), microspheres were loaded with GST-melittin and exposed a fraction to thrombin. *S. pyogenes* cells were exposed to protein released from microspheres in response to thrombin. GST-melittin loaded microspheres with activated thrombin inhibited *S. pyogenes* growth similarly to 10 μM synthetic melittin over a period of 12 hours. Protein released from microspheres without thrombin treatment had a limited growth inhibition (FIG. 20B).

Example 18

Discussion of Examples 16 and 17

The system reported above relies on enzyme activation as a release mechanism. As such, this system does not display burst kinetics during early release and mimics more closely natural defense mechanisms that need to be activated for effect. The mesh size of the hydrogel microspheres limited proteins from entering the microspheres, ensuring all protein association is with the surface of the microsphere (FIG. 17B). From the measurements of the size of the microspheres, a monolayer of dimeric GST-GFP would consist of approximately $2.6 \times 10^8$ molecules. In loading the microparticles with protein, PEGDA-Cys and PEGDA-GSH microspheres bound similar amounts of protein non-specifically. This may be predominantly in the associated water phase as this was significantly removed following washing. After washing the microspheres, PEGDA-GSH microspheres bound an order of magnitude more protein than the PEGDA-Cys microspheres indicating that a specific interaction was present allowing binding to the particles. The GST-GFP covering the surface of these microspheres was releasable by thrombin in both cases.

There are specific and non-specific interactions that allow the GST-GFP to bind to the microspheres, and the specific interactions appear to account for more than monolayer coverage of the microspheres. There are several possible reasons for the multilayer binding to the PEGDA-GSH microspheres. Pendent GSH moieties would be at a distance from the visible surface of the microsphere depending on the length of the growing acrylate backbone before GSH incorporation. Pendant chains extending beyond the surface would greatly increase the amount of protein bound, but not change the apparent size of the particles. GST-GFP could also partially enter the microsphere polymer mesh where the mesh is above the average value. The measured mesh size was based upon the bulk properties and the surface of the microspheres, particularly when loops, entangled loops, and dangling chains are present. The GSH bound to dangling chains would be present at a distance from the surface. These small changes would be expected to greatly increase the effective surface for binding. Based upon our results, it was clear that this multilayer is specifically binding.

To confirm the specificity, 10 mM GSH addition to PEGDA-GSH bound GST-GFP resulted in 50% protein elution from the microspheres in 48 hours and complete elution 6 days (FIG. 19). Low GSH concentrations did not release the protein from the microspheres, further suggesting that the interaction was specific. This was significant since whole blood (intracellular and plasma GSH) reduced GSH have been measured to be as high as 300 μg/mL, but plasma levels are significantly lower at 1.5 μg/mL, or 0.005 mM. Additionally, intracellular glutathione concentrations have been measured to be between 1 mM and 10 mM in healthy cells, and can be further increased in disease. The GST/GSH interaction would be expected to be stable periods of time at low glutathione levels allowing for release specifically in the presence of pathology associated proteases, including thrombin.

Thrombin mediated release of GST fusion proteins was significantly faster than elution, with an apparent $V_{max}$ of 0.13 μg/min. This maximum velocity was achieved with thrombin concentrations necessary for clot formation (100 nM). Interestingly, association with PEGDA microspheres significantly increased the apparent $K_m$ of thrombin to GST-GFP (FIG. 19A). In enzymatic terms, an upward shift in $K_m$ was indicative of an enzyme's reduced affinity for its substrate. In this case, the reduced affinity may be due to unfavorable, rigid or steric limitations of the GST-GFP substrate on the surface of the PEGDA microsphere. This phenomena may be a modifiable parameter that may allow for more refined control of protein release from immobilized GSH containing hydrogels.

Finally, it was shown that GST-melittin can be loaded to the PEGDA-GSH microspheres as efficiently as GST-GFP (FIG. 20A), and that S. pyogenes growth was inhibited by melittin cleaved from PEGDA-GSH microspheres by thrombin. Thrombin is upregulated during bacterial infection, and the uncontrolled upregulation of thrombin during infection can lead to a lethal condition known as disseminated intravascular coagulation. Thrombin was, therefore, deemed an appropriate enzyme to be used for activation of anti-bacterial coatings. This would be particularly true for blood-contacting materials.

Under these conditions, the melittin released from microspheres estimated to contain melittin to achieve 1 μM when released was approximately as effective at inhibiting S. pyogenes cell growth as 1 μM synthetic melittin (FIG. 20B). Based upon the growth inhibition, melittin can be loaded predictably on hydrogel microparticles and activated by thrombin. The loaded melittin inhibited growth of high concentrations of pathogenic S. pyogenes cells. These densities of S. pyogenes cells would be clinically encountered during active infection, and suggested that the delivery potential of GST-melittin from surface coated material would find further utility as a treatment for active infection.

It is shown herein that GSH immobilized on the surface of PEGDA microspheres specifically and predictably interacted with GST fused GFP and melittin. The interaction was stable under extracellular salt and GSH conditions. Further, thrombin released proteins fused to the GST and allowed them to exert activity. Melittin was released from the surface and was as functional as synthetic melittin at a similar concentration in inhibiting the growth of pathogenic S. pyogenes.

Example 19

Polypeptide Delivery in a Mouse Angiogenesis Model

PEGDA:GSH hydrogel is loaded with one or more GST-polypeptide fusions having a cleavage site for matrix metalloprotease-9 between GST and the polypeptide. Matrix metalloprotease-9 (MMP-9) recognizes the cleavage site having the amino acid sequence GPLGVRGS (SEQ ID NO:5). The loaded hydrogel is implanted in a mouse angiogenesis model to assess the bioactivity of the released polypeptides. Particularly, the polypeptides eGFP (i.e., Green Fluorescent Protein), mCherry (Red Fluorescent Protein), and a cell lytic polypeptide having the amino acid sequence KWKLFKKIGAVLKVL (SEQ ID NO:3) are examined in this angiogenesis model.

Specifically, mice are administered an intraperitoneal injection of ketamine and xylazine (100 mg/kg and 5 mg/kg, respectively), and an injection site is rubbed with 75% ethanol. Anesthesia is indicated by a toe pinch reflex test. All instruments are autoclaved prior to use and standard aseptic technique is followed for the procedure as detailed below.

The treatment groups include PEGDA:GSH hydrogel loaded with eGFP, mCherry, or the cell lytic polypeptide, each being linked to GST via the amino acid sequence containing the cleavage site recognized by MMP-9. Additionally, the treatment groups are further segregated into mice receiving GM6001 or mice not receiving GM6001. GM6001 is an inhibitor of matrix metalloproteases. Each treatment group includes 6 female C57BL/6 mice at 3-4 weeks of age (i.e., 10-15 g).

Two incisions (about 0.5 cm to about 1.0 cm each) are made on a dorsal surface of each mouse. Hydrogel (about 3 mm in diameter and about 5 mm thick) from each respective treatment group is inserted into the subcutaneous space formed using a blunt probe for each incision. Particularly, two hydrogels for each treatment group are inserted per mouse, one hydrogel on the left side of the back and the other hydrogel on the right side of the back. For the mice receiving GM6001, GM6001 is administered intraperitoneally at a concentration of 0.1 mg/g in 4% (w/v) carboxymethylcellulose in water. The GM6001 is administered once daily for two weeks.

After 14 days, the inserted hydrogels are removed for whole mount immunostaining to determine the number of blood vessels per area formed in the hydrogel. The hydrogel itself is visualized by H&E stain. Particularly, after one-hour of blocking, the hydrogel is incubated with anti-CD31 antibody overnight at 4 degrees Celsius to allow for fluorescence imaging of the endothelium formed about and/or within the hydrogel. After incubation with a secondary antibody, the hydrogel is mounted under a fluorescent microscope for quantization of vessels.

Positive controls (e.g., mice not receiving GM6001, but receiving eGFP or mCherry via hydrogel) are significantly vascularized while mice receiving GM6001 have limited vessel growth as GM6001 inhibits angiogenesis. The cell lytic polypeptide inhibits vascularization of the hydrogel.

Example 20

Materials and Methods for Example 21

Hydrogel Microparticle Formation. Microparticles are formed by polymerizing PEGDA and acrylic acid on a wire mesh between two glass slides. The particles are about 500 microns in diameter and about 170 microns in thickness. Free radical initiation using APS and TEMED are used to polymerize the hydrogel particles.

Surface Modification of the Hydrogel Microparticle. Solvent and temperature differences between hydrogels and reaction mixture were used to control selective modification of exterior free carboxyl groups.

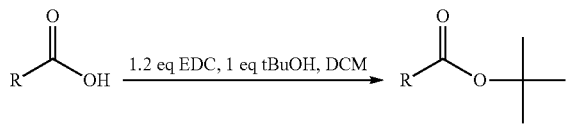

FTIR Spectroscopy. Interior and exterior chemistries of the hydrogels were analyzed by scanning the surface of the hydrogels for the exterior chemistry and slicing the hydrogels to scan the interior chemistry.

XPS. A modified MMP-cleavable peptide, G-(4-iodo)-F-PLGVRG(SEQ ID NO:11)-NH2, was selectively conjugated to the interior of the particles, and XPS analysis for the iodine peak was done on the surface and the interior of these particles.

Fluorescence Spectroscopy. TAMRA-tagged MMP-cleavable peptide, TAMRA-GPLGVRG(SEQ ID NO:12)-$NH_2$, was selectively conjugated to the interior of the hydrogels. Release studies using free-MMP were done, by incubating gels in Tris/Zn buffer. Fluorescence readings were collected at specific time-points.

Example 21

Characterization of Surface Modified Microparticles

Figure 21:
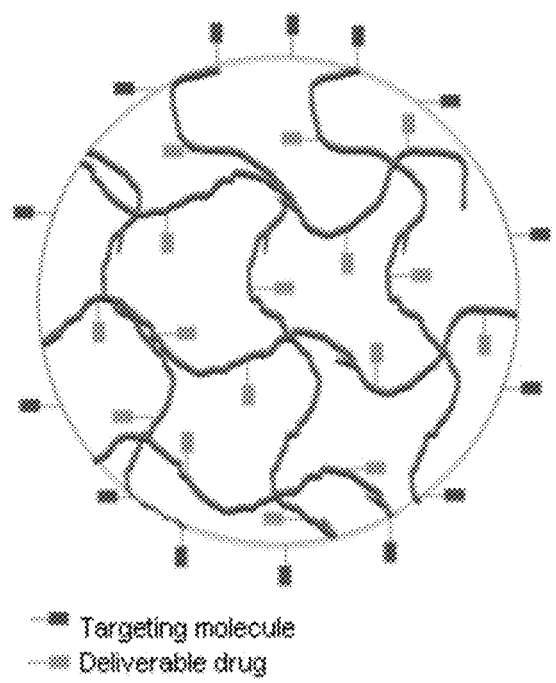
FIG. 21 shows a hydrogel, in which the surface chemistry of the hydrogels is different from the interior chemistry of the hydrogel.
Figure 22:
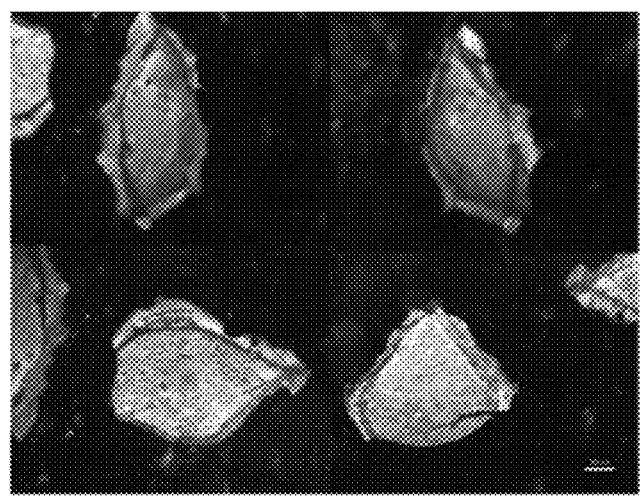
FIG. 22 shows microparticles polymerized using a wire mesh are 500 microns in diameter and 170 microns in thickness.
Figure 23:
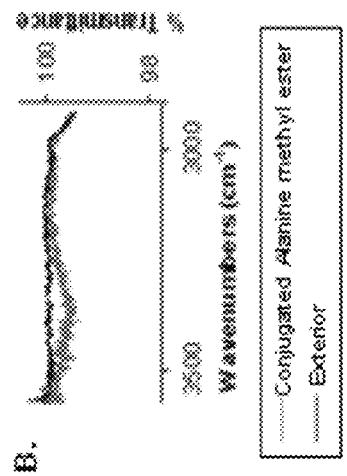
FIG. 23 shows FTIR analysis of hydrogel chemistries. (A) FTIR of surface esterified hydrogels (exterior and interior chemistries) is compared to unmodified hydrogels. (B) Alanine methyl ester is conjugated to a surface esterified hydrogel, and interior conjugation is confirmed.
Figure 23A:
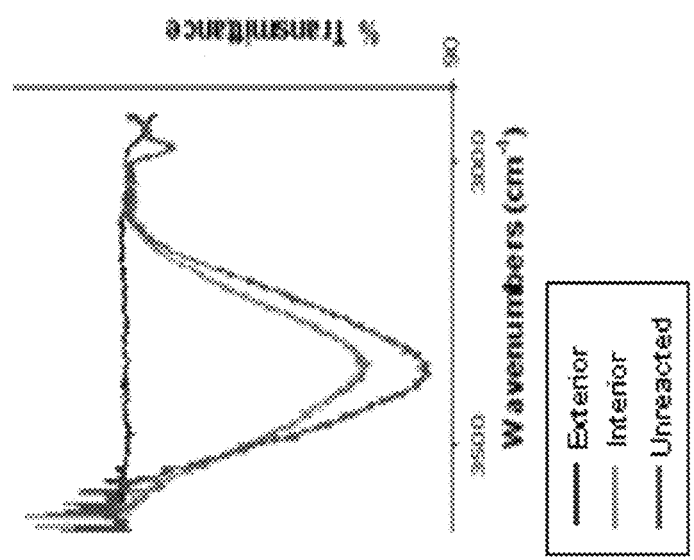
Figure 24:
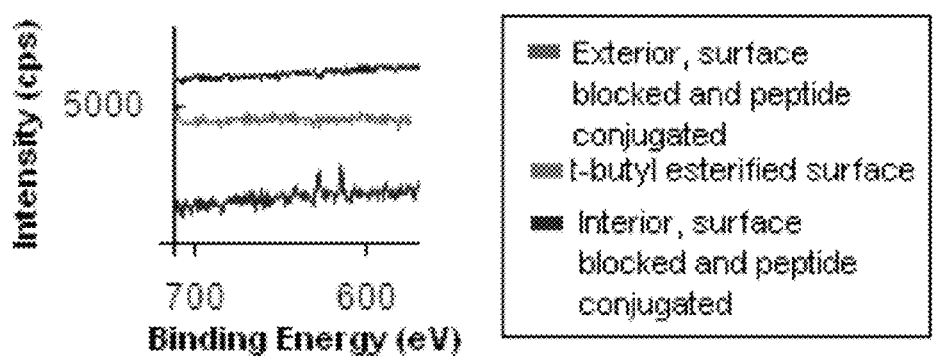
FIG. 24 shows XPS spectrum of modified hydrogels with and without peptide conjugation in comparison to surface modified hydrogel without peptide conjugation. Selective modification of our particles is confirmed, by showing that the iodine containing peptide is conjugated only on the interior, and not on the exterior.
Figure 25:
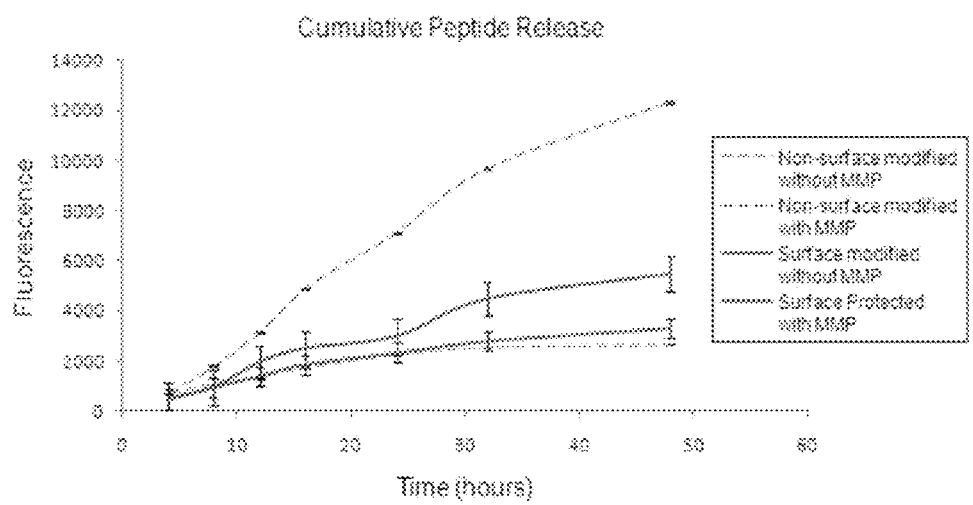
FIG. 25 shows MMP directed peptide release over time for surface modified hydrogels and non-surface modified hydrogels. MMP cleavable peptide release is measured in surface modified hydrogels by fluorescence intensity of reaction buffer from 0-48 hours. Peptide release is compared to nonspecific release without MMP cleavage. MMP peptide release is measured in unmodified hydrogels. Both specific and nonspecific release are shown.

The surface of PEGDA/acrylic acid hydrogel microparticles was selectively modified to place a targeting molecule on the surface. The microparticles were 500 microns in diameter and 170 microns in thickness (FIG. 22). A cleavable peptide was attached to an interior of the surface modified hydrogel and matrix metalloprotease (MMP) was used to actively release such a peptide from the hydrogel (FIG. 21). These surface modified hydrogels were characterized by FTIR (FIG. 23) and XPS (FIG. 24), thereby confirming surface modification of the microparticles. The rate of peptide release in the presence of MMP and/or surface modification was measured for 48 hours. Peptide release by MMP was slower in the presence of surface modifications on the hydrogel microparticles.

These modified hydrogel systems can be used as tunable drug delivery vehicles by modifying chemical identity, density, and location or hydrogel composition. It was shown that an overactived enzyme in cancers, matrix-metalloprotease (MMP), can activate a delayed release from these gels, as compared to unmodified hydrogel systems. A lag in time for the MMP to pass through surface modified region, enter the hydrogel, and begin cleavage demonstrated that (i) there was surface modification of the hydrogel microparticles, (ii) MMP did enter the hydrogel microparticle, and (iii) MMP cleavable peptides can be used as drug activators in hydrogel microparticle system.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A hydrogel composition for in vivo drug delivery comprising:
   a polymer covalently linked to glutathione (GSH) with therapeutic polypeptide molecules bound to the hydrogel by glutathione S-transferase (GST) fusion partners.

2. The hydrogel composition of claim 1, wherein said polymer includes monomers and one or more of said monomers within said polymer covalently linked to glutathione are addition polymerization monomers that are hydrophilic.

3. The hydrogel composition of claim 2, wherein said addition polymerization monomers are poly(ethylene glycol) diacrylate (PEGDA).

4. The hydrogel composition of claim 3, wherein a ratio of acryl monomer to GSH is from 1:1 to 10:1.

5. The hydrogel composition of claim 1, wherein the one or more therapeutic polypeptide molecules are covalently linked to glutathione S-transferase (GST).

6. The hydrogel composition of claim 5, wherein said therapeutic polypeptides are linked to GST via a recognition site for a protease.

7. The hydrogel composition of claim 6, wherein the protease is thrombin.

8. The hydrogel composition of claim 1, wherein the therapeutic polypeptide molecules are released by intracellular glutathione.

9. The hydrogel composition of claim 6, wherein said polypeptide molecule is melittin.

10. The hydrogel composition of claim 6, wherein the one or more therapeutic polypeptide molecules are selectively released from the hydrogel via a disease-selective protease.

11. The hydrogel composition of claim 9, wherein the protease is thrombin.

12. The hydrogel composition of claim 1, wherein the disease promotes the presence of a protease at the localized delivery site, thereby linking a rate of release of the one or more therapeutic polypeptide molecules from the hydrogel to the disease.

13. A hydrogel having a composition for in vivo drug delivery comprising:
   a polymer covalently linked to glutathione (GSH) with therapeutic proteins bound to the interior of the hydrogel by glutathione S-transferase (GST) fusion partners and at least one additional polypeptide bound only to a surface of the hydrogel through GSH-GST interactions.

14. The hydrogel composition of claim 13, wherein one or more therapeutic polypeptide molecules are immobilized on a surface of the hydrogel.

15. The hydrogel composition of claim 13, wherein the polypeptide is isolated to the surface of the hydrogel by the mesh size of the hydrogel being smaller than the hydrodynamic radius of the polypeptide.

16. The hydrogel composition of claim 13, wherein the one or more of said therapeutic polypeptide molecules immobilized on the surface are cell-selective polypeptides.

17. The hydrogel composition of claim 13, wherein the disease promotes the presence of the protease at the localized delivery site, thereby linking a rate of release of the one or more agents from the hydrogel interior or surface to the disease.

* * * * *

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 1

Leu Val Pro Arg
1

<210> SEQ ID NO 2
<211> LENGTH: 25
<212> TYPE: PRT
<213> ORGANISM: Artificial Sequence
<220> FEATURE:
<223> OTHER INFORMATION: Synthetic polypeptide
```

-continued

```
<400> SEQUENCE: 2

Gly Ile Gly Ala Val Leu Lys Val Leu Thr Thr Gly Leu Pro Ala Leu
1               5                   10                  15

Ile Ser Trp Ile Lys Arg Lys Arg Gln
            20                  25

<210> SEQ ID NO 3
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 3

Lys Trp Lys Leu Phe Lys Lys Ile Gly Ala Val Leu Lys Val Leu
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 4

Cys Asn Tyr Tyr Ser Asn Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 5

Gly Pro Leu Gly Val Arg Gly Ser
1               5

<210> SEQ ID NO 6
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 6
ccatgggcag cagccatcat cat                                           23

<210> SEQ ID NO 7
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 7
agctggaatt cctagttatt gctcagcggt ggc                                33

<210> SEQ ID NO 8
<211> LENGTH: 71
<212> TYPE: DNA
<213> ORGANISM: Artificial Sequence
<220> FEATURE:
<223> OTHER INFORMATION: Synthetic polynucleotide
```

```
<400> SEQUENCE: 8
aaaggatcca tcatcatcat catcatggtc cgctgggcgt tcgtggtatg gctagcaaag      60
gagaagaact c                                                           71

<210> SEQ ID NO 9
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 9
aaagaattct cagttgtaca gttcatccat gccatg                                36

<210> SEQ ID NO 10
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 10
agcggatccg gtatcggtgc tgttctgaaa gttctgacca ccggtctgcc ggctctgatc      60
tcttggatca aacgtaaacg tcagtaggaa ttctcacg                              98

<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 11

Pro Leu Gly Val Arg Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 12

Gly Pro Leu Gly Val Arg Gly
1               5
```